(12) United States Patent
Botimer

(10) Patent No.: US 7,722,615 B2
(45) Date of Patent: May 25, 2010

(54) EXPANDABLE SURGICAL REAMING TOOL

(76) Inventor: Gary Botimer, 13753 Locust La., Nampa, ID (US) 83686

( * ) Notice: Subject to any disclaimer, the term of this patent is extended or adjusted under 35 U.S.C. 154(b) by 467 days.

(21) Appl. No.: 11/440,712

(22) Filed: May 24, 2006

(65) Prior Publication Data

US 2007/0016211 A1    Jan. 18, 2007

Related U.S. Application Data

(63) Continuation-in-part of application No. 11/137,123, filed on May 24, 2005.

(60) Provisional application No. 60/749,968, filed on Dec. 12, 2005.

(51) Int. Cl.
*A61B 17/00* (2006.01)

(52) U.S. Cl. .......................... 606/81; 606/80

(58) Field of Classification Search ........... 606/80, 606/81
See application file for complete search history.

(56) References Cited

U.S. PATENT DOCUMENTS

| | | | |
|---|---|---|---|
| 3,702,611 A | 11/1972 | Fishbein | 128/305 |
| 5,116,339 A | 5/1992 | Glock | 606/91 |
| 5,203,653 A | 4/1993 | Kudla | 408/207 |
| 5,376,092 A | 12/1994 | Hein et al. | 606/81 |
| 5,462,548 A | 10/1995 | Pappas et al. | 606/80 |
| 5,527,316 A | 6/1996 | Stone et al. | 606/80 |
| 5,755,719 A | 5/1998 | Frieze et al. | 606/81 |
| 5,830,215 A | 11/1998 | Incavo et al. | 606/79 |
| 5,897,558 A | 4/1999 | Frieze et al. | 606/81 |
| 5,919,195 A | 7/1999 | Wilson et al. | 606/80 |
| 6,106,536 A | 8/2000 | Lechot | 606/180 |
| 6,224,604 B1 * | 5/2001 | Suddaby | 606/80 |
| 6,283,971 B1 | 9/2001 | Temeles | 606/81 |
| 6,383,188 B2 | 5/2002 | Kuslich et al. | 606/80 |
| 6,656,187 B1 | 12/2003 | Camino | 606/85 |
| 6,755,865 B2 | 6/2004 | Tarabishy | 623/22.12 |
| 6,783,533 B2 | 8/2004 | Green et al. | 606/80 |

FOREIGN PATENT DOCUMENTS

DE    38 40 466 A1 *  6/1990

* cited by examiner

*Primary Examiner*—Eduardo C Robert
*Assistant Examiner*—Juliana N Harvey
(74) *Attorney, Agent, or Firm*—Pedersen and Co., PLLC; Ken J. Pedersen; Barbara S. Pedersen

(57) ABSTRACT

An expanding reamer prepares an acetabulum for a prosthetic component during hip arthroplasty. One or more blades expand in directions non-parallel to the plane of the respective blades and form an effective cutting sphere preferably greater-than-180-degrees for greater flexibility in placement of the reamer shaft relative to the center of axis of the acetabulum. Two parallel blades may move out away from each other and from the reamer rotational axis, staying parallel to each other to become more distanced, but still parallel, segments of a larger cuffing sphere. Or, two blades may start generally parallel to each other and to the rotational axis of the device, but pivot out from each other in directions generally perpendicular to their respective blade planes, again becoming more distanced, but not parallel, segments of a larger cuffing sphere.

12 Claims, 29 Drawing Sheets

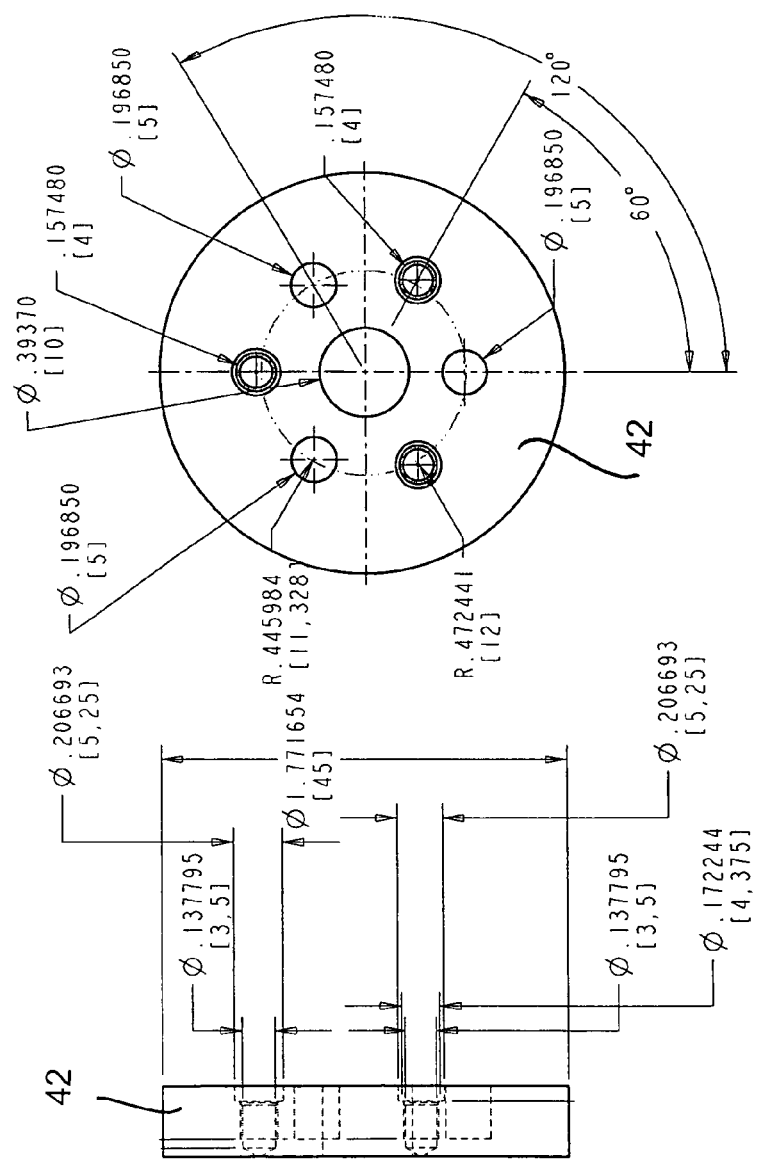
*Fig. 8C*
*Fig. 8B*
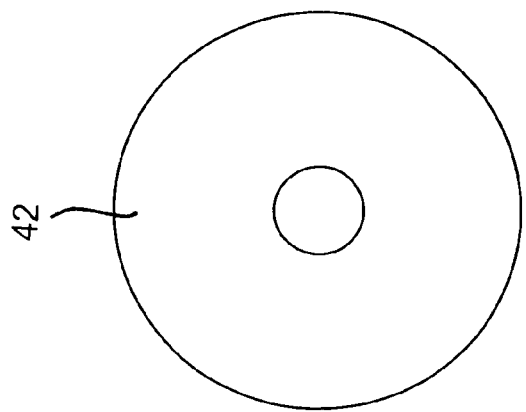
*Fig. 8A*

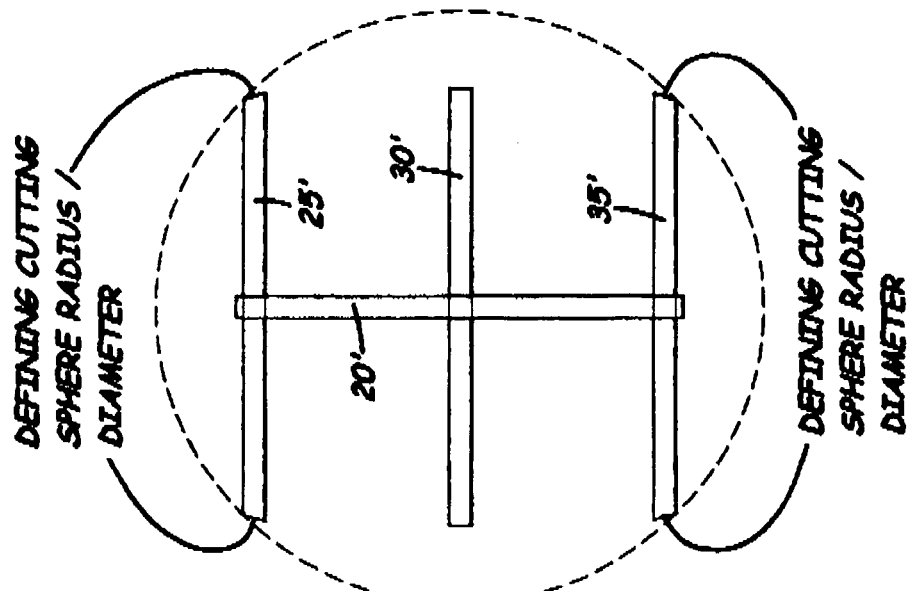
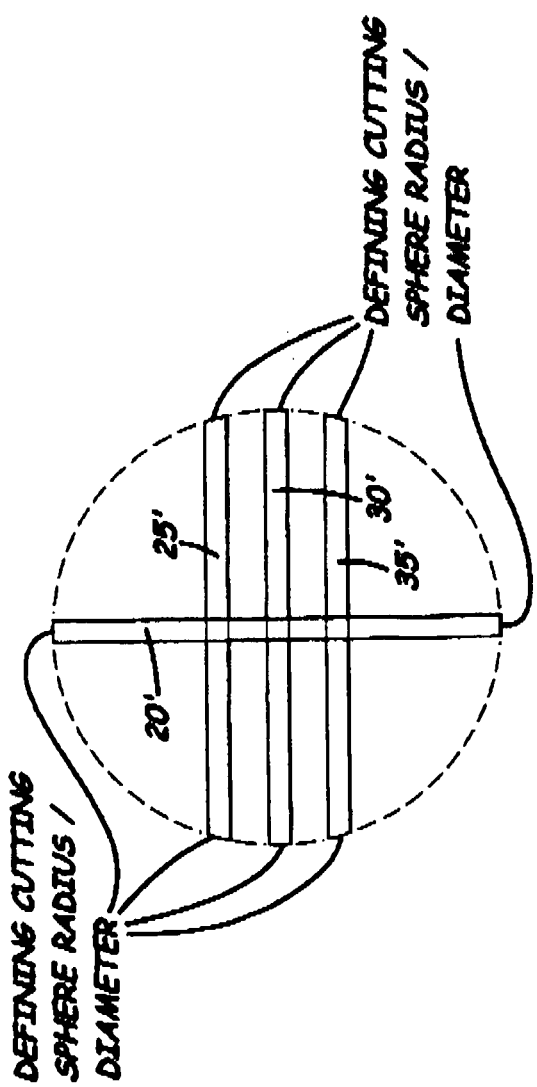
Fig. 17B
Fig. 17A

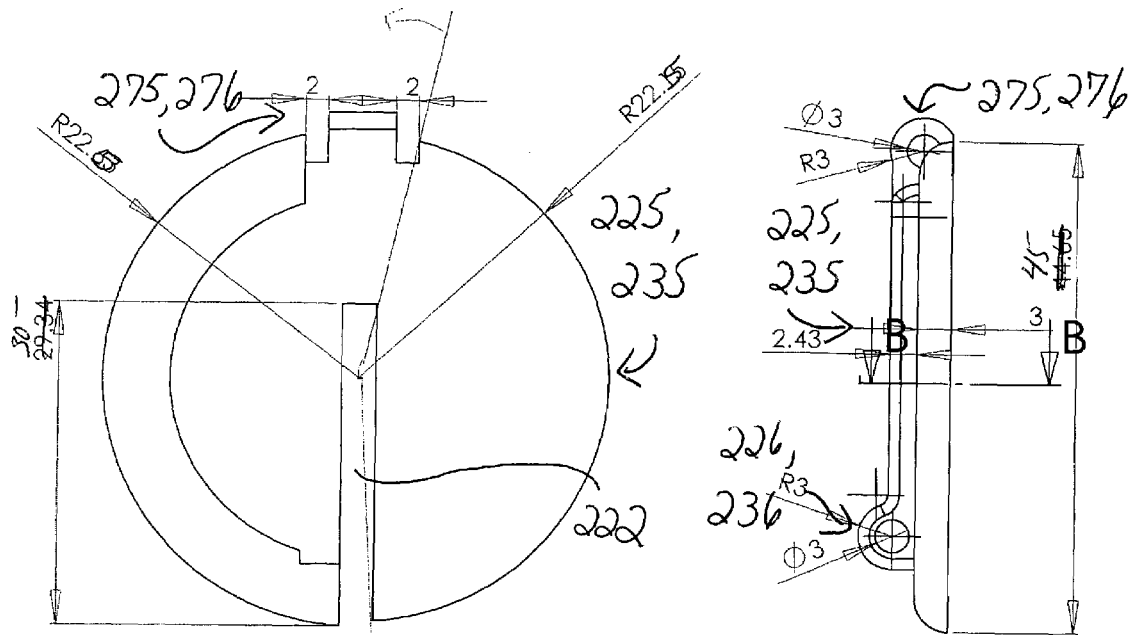
figure 25A
figure 25B
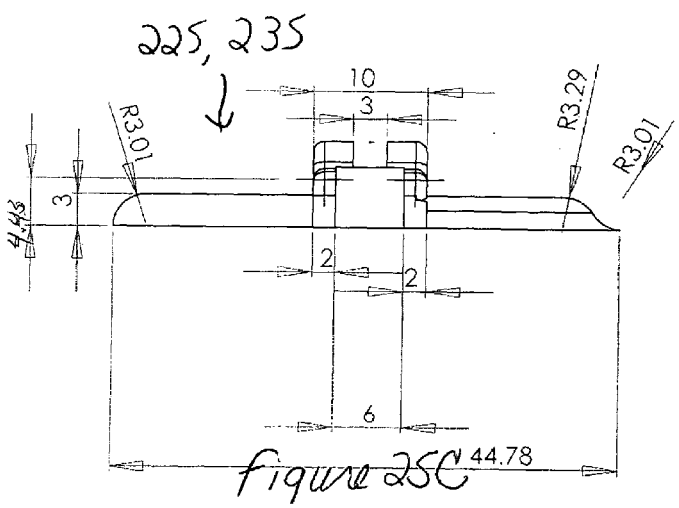
figure 25C
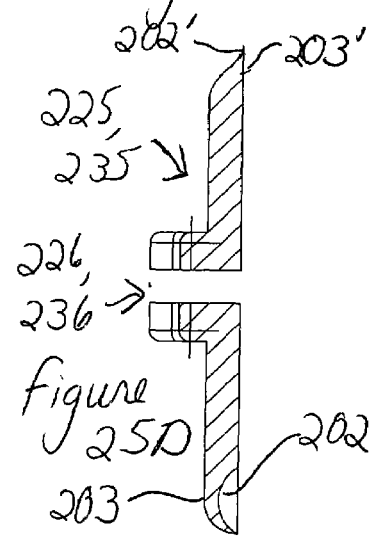
figure 25D

Spherical Cap

Radius of sphere: r
Radii of base: $r_1$

Height: h
Surface area: S
Volume: V

Segment and Zone of a Sphere

Radius of sphere: r
Radii of bases: $r_1$, $r_2$

Height: h
Surface area: S
Volume: V

EXPANDABLE SURGICAL REAMING TOOL

This application claims priority of U.S. application Ser. No. 11/137,123, filed May 24, 2005, and also claims priority of and incorporates by this reference U.S. application Ser. No. 60/749,968, filed Dec. 15, 2005.

BACKGROUND OF THE INVENTION

1. Field of the Invention

The present invention relates generally to a reaming device and, more particularly, to an expandable reaming device that may be used for reaming an acetabulum in preparation for implanting a prosthetic component, such as an acetabular cup or socket during a hip arthroplasty.

2. Related Art

The hip joint is a ball-and-socket joint formed by the articulation of the rounded, convex surface of the head of the femur with the cuplike acetabulum on the pelvis. In a healthy hip joint, the head of the femur and the acetabulum are lined by surface cartilage; the entire joint is surrounded by a capsule which has a thin lining of synovial cells that produce a thin layer of lubrication film called synovial fluid. The synovial fluid, together with the cartilage, acts as a shock absorber and allows the joint to move. If the surface cartilage is badly damaged, or if the joint surfaces are not aligned properly, then the cartilage will wear out, and as a result, the bone under the cartilage layer is exposed. The exposed bone starts to rub against each other and the process of osteoarthritis is established.

Osteoarthritis is the result of mechanical wear and tear on a joint, in this case, the hip joint. The main indication is a loss of surface cartilage due to the bone rubbing on bone. The formation of bone spurs, called osteophytes and cysts around the joint is another indication of osteoarthritis. The body tries to relieve the pain from the rubbing of the bone by increasing the amount of fluid in the joint. In an arthritic hip, the cartilage lining is thinner than normal or completely absent; the capsule of the arthritic hip is swollen; the joint space is narrowed and irregular in outline; and/or excessive osteophytes can build up around the edges of the joint. The combination of these factors cause pain and will eventually result in the loss of motion of the hip.

Hip arthroplasty is a surgery performed to replace all or part of a joint, deteriorated from osteoarthritis, with an artificial device in order to restore joint movement. There are different types of hip arthroplasty. If a hemi-arthroplasty is performed, either the femoral head or the acetabulum is replaced with a prosthetic device. In a total hip arthroplasty, both the femoral head and the acetabulum are replaced with prosthetic devices. Hip arthroplasty involves reforming the patient's natural acetabulum, so that a proper bearing surface for the ball of a femur is established in order to support the normal motion of the leg. The acetabulum needs to be reshaped so that it can properly receive a metallic or plastic artificial socket; typically osteophytes and other deteriorated and diseased bone are removed from within and around the acetabulum using a bone chisel, until healthy bone becomes visible. Typically, a reamer is used to accomplish this reshaping of the acetabulum, and reamer heads of increasingly larger size are required as bone is cut away and the socket is enlarged. Each time a larger reamer head is needed, the reaming system must be removed from the patient's acetabulum, the reamer head is removed from the drive shaft of the surgical drill, and the next larger reamer head is attached. This sequence may be repeated several times until the acetabulum is completely prepared to receive an acetabular prosthetic implant. The process of replacing reamer heads multiple times during a surgery is time consuming, inefficient, inconvenient, and may also lead to surgical errors in that the angle of acetabular penetration may not be accurately preserved during each reamer head substitution.

Standard hip arthroplasty is typically performed using a posterolateral or anterolateral approach, with an incision of 25-30 cm in length (see FIG. 1A). The approach provides substantial exposure, and complete and continuous observation, of the hip. With this large incision, it is unlikely that the reamer will be off axis. However, this exposure comes at the expense of trauma to the muscle and tendons and of considerable postoperative pain, requiring inpatient stay and delay of postoperative physical therapy.

Recently, minimally invasive (MIS) hip arthroplasty has been used as an alternative. MIS hip arthroplasty approaches include single-incision and 2-incision techniques, wherein each incision measures about 10 cm in length (see FIG. 1B). With the MIS techniques, a decrease in muscle and tendon trauma is achieved at the expense of not having complete and continuous observation of the hip. With a small incision, it is more difficult to place the acetabular reamer in direct alignment with the axis of the acetabulum. If the smaller incision is not exactly aligned with the acetabulum (see FIG. 2A), the reamer will be off axis relative to the axis of the acetabulum. If the reamer is off axis and the head of the reamer has hemispherical or less cutting capability ("180 degrees or less head"), it will be unable to cut a perfect hemisphere in the acetabular space (see FIG. 2B). A portion P of the acetabular space will be improperly reamed, or, more likely, not reamed at all. Therefore, the inventor believes that there is still a need for an acetabular reamer that is expandable to eliminate the need for multiple reamers and a reamer head that is greater than 180 degrees to allow the surgeon to cut a perfect hemisphere even when the reamer is off axis.

Issued patents relating to expandable acetabular reaming devices include the following:

Fishbein (U.S. Pat. No. 3,702,611) discloses an expanding reamer including a head with a convex end adapted to seat in a previously-prepared concavity in the central part of the acetabulum; the head pivotally mounts a set of expansive blades and is telescopically mounted on the end of a rotary drive shaft.

Temeles (U.S. Pat. No. 6,283,971) discloses an expandable acetabular reaming system having a plurality of blades that project or retract through a reamer head according to a desired reamer head size. The degree projection or retraction of the reaming blades is manually controlled by user actuation of an air bladder.

SUMMARY OF THE INVENTION

The present invention relates to an expandable reaming device for reaming, cutting, or drilling, which has one or more moveable blades for increasing the effective diameter of the reamer head. The expandable device may be adapted for reaming an acetabulum in preparation for implanting a prosthetic component, such as an acetabular cup or socket, during a hip arthroplasty. The preferred reaming device comprises blades or blade portions that, individually or together, provide a greater-than-180-degree cutting edge(s), so that, upon rotation of the reamer head, the device may ream a hemisphere in a surface even if the rotational axis of the device is not parallel to the axis of the concave surface being reamed/cut. During a hip arthroplasty, this offers greater flexibility in placement of the shaft of the reaming device relative to the center of axis of the acetabulum, and, hence, is advantageous for MIS hip arthroplasty Preferred embodiments of the invention comprise at least one generally plate-shaped cutting blade that acts as a segment of a sphere, wherein the reamer head is expandable to a greater cutting diameter by said segment being moved in a direction that is non-parallel to the plane of the segment. Thus, said segment becomes a segment of a sphere with a greater diameter, and, hence, reams to a larger diameter, preferably a larger hemisphere or greater-than-hemisphere.

Preferably, said at least one blade is positioned so that its plane is generally parallel to the rotational axis of the reaming device, so that, upon rotation around the central axis, the blade cuts a sphere/partial sphere. Moving the cutting blade out in a direction exactly or substantially perpendicular to its plane makes the blade serve, without enlarging the diameter of the blade, as a segment of a larger sphere, and, hence, upon further rotation around the rotational axis of the device, it reams/cuts a larger sphere/partial sphere. Thus, instead of pivoting or tipping a blade out in a plane parallel to its own blade plane, as in several of the reaming heads of the prior art, the invented blade moves in a direction non-parallel, and preferably generally perpendicularly, to its own plane and reams/cuts a perfect or nearly perfect sphere or partial sphere. "Generally perpendicularly" may range from exactly perpendicularly to substantially perpendicularly, wherein the major vector of movement of the blade from its starting/contracted position is in a direction perpendicular to the blade plane. Included in substantially perpendicularly is a blade that starts generally parallel to the rotational axis and pivots out and down at its top in a direction perpendicular to the blade plane.

Many embodiments of the reaming device comprise a drill bit on a rotating shaft for cooperating with a surgical drill or other power unit, a plurality of blades connected directly or indirectly to the rotating shaft, and a gearing system or other actuation system adapted to expand the moveable blades.

In one preferred embodiment, the moveable, "expanding blade(s)" comprise two parallel blades that remain parallel to each other and to the rotational axis throughout expansion, the blades each being greater than 180 degrees in circumference and each generally forming a segment of a sphere. As the expanding blades move outward, perpendicularly to their respective blade planes, the effective diameter of the reaming head increases and the reaming head may ream/cut increasingly larger-diameter partial spheres. The expanding blades are preferably raised as they are moved outward, to maintain the effective reaming/cutting shape of the reaming head very close to a perfect partial sphere.

The two expanding blades may be located on either side of, and parallel to, a central blade passing through the axis of rotation of the device. A transverse blade is preferably positioned perpendicular to the expanding blades and the central blade, and centered so that it also passes through the axis of rotation of the device. The central blade and/or the transverse blade may also be used for reaming/cutting, especially reaming/cutting of the bottom region of the concave surface being formed, and especially after the moveable blades have been expanded outward. The preferred expanding blades move out along the transverse blade, guided by ramps in or on the transverse blade that raise the blades at the same time they are expanding.

In an alternative embodiment, two expanding blades start, when the reamer head is contracted, generally parallel to the rotational axis of the device, and then expand by pivoting out and down generally perpendicularly to their respective blade planes. Thus, the two blades, at the start of reaming, are generally parallel, and are pivoted generally outward during expansion to become non-parallel to each other and non-parallel to the rotational axis. The blades preferably are each greater than 180 degrees in circumference and each generally form a segment of a sphere. As the expanding blades move outward, the effective diameter of the reaming head increases and the reaming head may ream/cut increasingly larger-diameter partial spheres. The expanding blades maintain the effective reaming/cutting shape of the reaming head very close to a perfect partial sphere throughout expansion.

In the pivoting blade embodiment, a transverse blade(s) is(are) preferably positioned perpendicularly to the expanding blades, and centered to pass through the axis of rotation of the device. The transverse blade(s) may serve as support guides for the moveable/expandable blades, and may also contribute a reaming/cutting edge(s). For example, when the reamer head is fully-contracted, a substantial portion of the transverse blade edge preferably will be positioned where it will ream/cut, thereby supplementing the action of the moveable blade cutting edges. After expansion, as the transverse blade preferably does not expand, the transverse blade will typically cut only a small portion of the bottom region of the concave surface being formed, while the expandable blades will cut the majority of the concave surface being formed.

BRIEF DESCRIPTION OF THE DRAWINGS

In the following drawings, gear teeth and threads are not drawn, but are understood when parts are described by the terms "gear", "teeth", "threads," "threaded," "toothed surfaces," or "threaded surfaces."

FIG. 8A is a bottom view of the bottom plate of the embodiment shown in FIGS. 3-7.

FIG. 8B is a side view of the bottom plate of the embodiment shown in FIGS. 3-8A.

FIG. 8C is a top view of the bottom plate of the embodiment shown in FIGS. 3-8B.

FIG. 17A is a schematic top cross-sectional view of a fully-contracted reamer head, showing in dashed lines the effective cutting diameter of the head.

FIG. 17B is a schematic top cross-sectional view of the reamer head of FIG. 17A (same size and same diameter blades) in a fully-expanded condition, again showing in dashed lines the larger effective cutting diameter of the head.

FIG. 25A is a view of an expanding blade of the reamer of FIGS. 19-23.

FIG. 25B is a side edge view of the blade of FIG. 25A.

FIG. 25C is a top edge view of the blade of FIGS. 25A and B.

FIG. 25D is a cross-sectional view of the blade of FIGS. 25A-25C, viewed along the line 25D-25D in FIG. 25B.

DESCRIPTION OF THE PREFERRED EMBODIMENTS

Referring to the figures, there are shown several, but not the only, embodiments of the invented expandable reaming device. While the preferred embodiments are especially-well adapted for reaming an acetabulum in hip arthroplasty, the preferred or other embodiments may be useful for other reaming, cutting, and drilling applications, both in the human body, animals, and/or other applications including non-surgical applications. Therefore, the terms "reaming," "cutting," and "reaming device" are not intended to limit the invented device to a particular medical procedure.

Figure 1A:
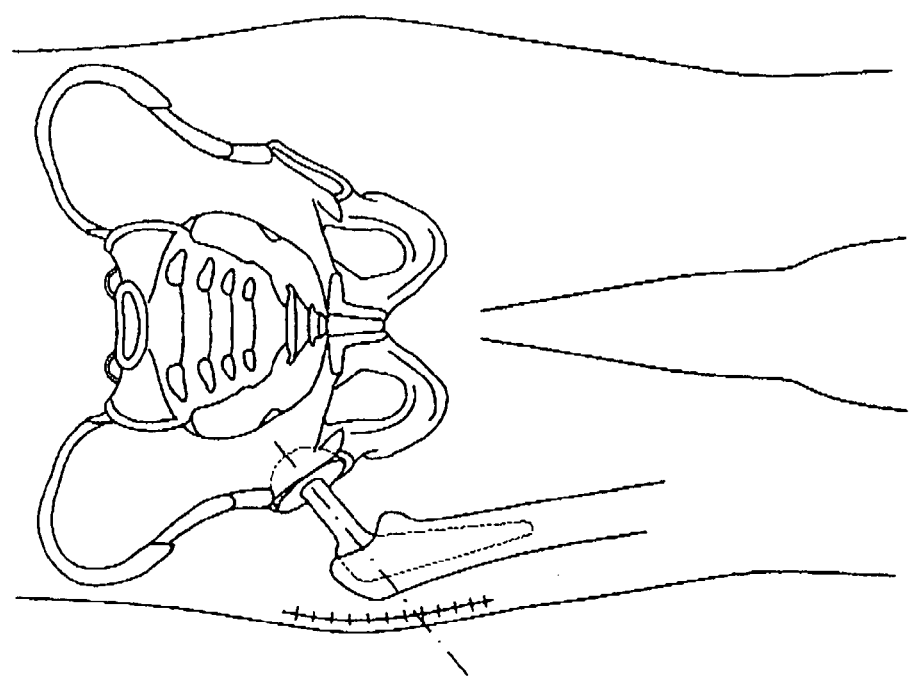
FIG. 1A is a front/anterior view of the standard incision made during a total hip arthroplasty.
Figure 1B:
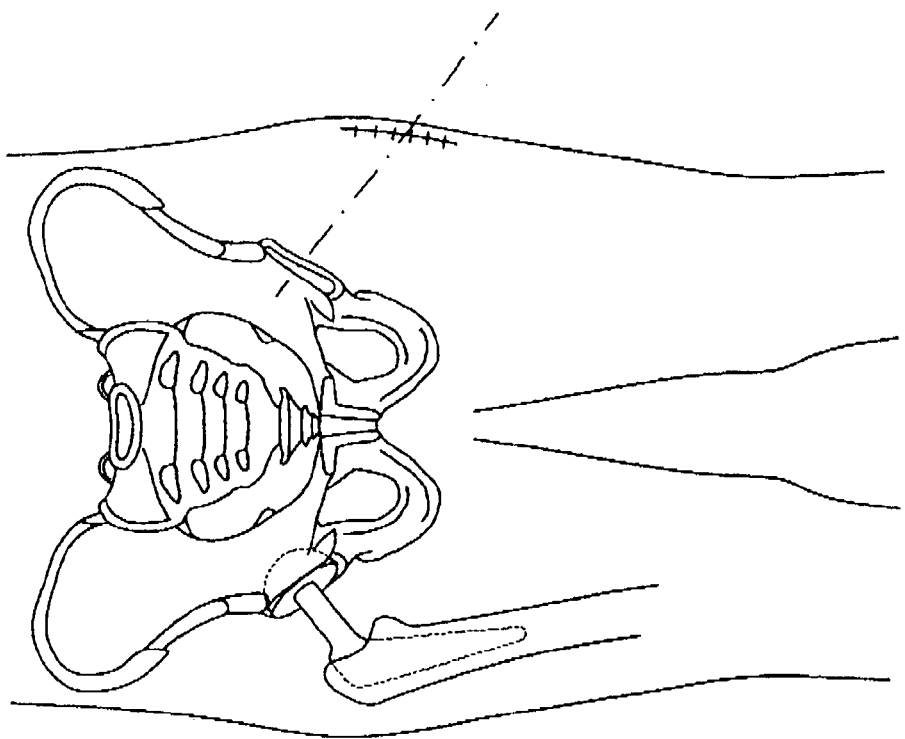
FIG. 1B is a front/anterior view of the new incision made during a minimally invasive total hip arthroplasty.
Figure 2A:
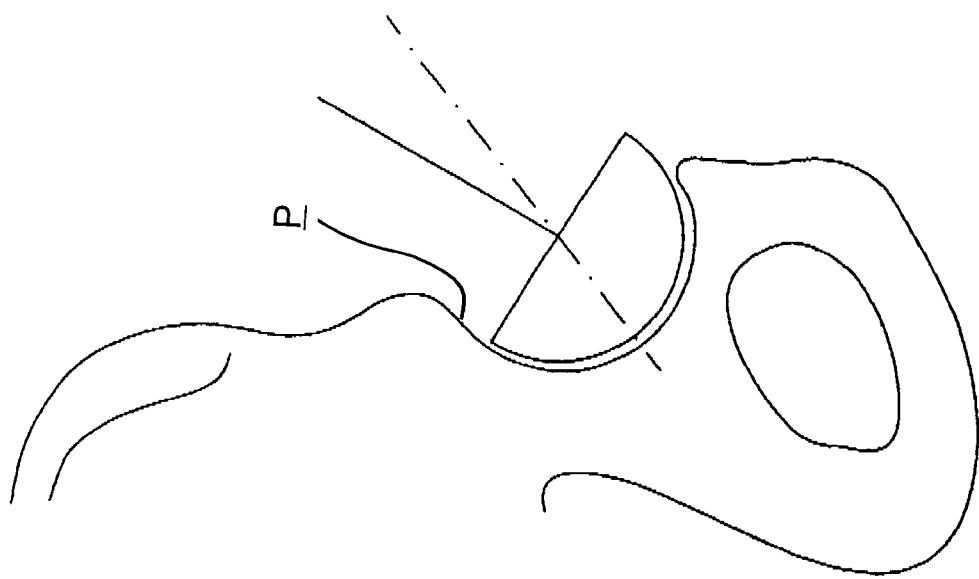
FIG. 2A is a schematic illustrating the standard acetabular reamer when the reamer is aligned with the axis of the acetabulum.
Figure 2B:
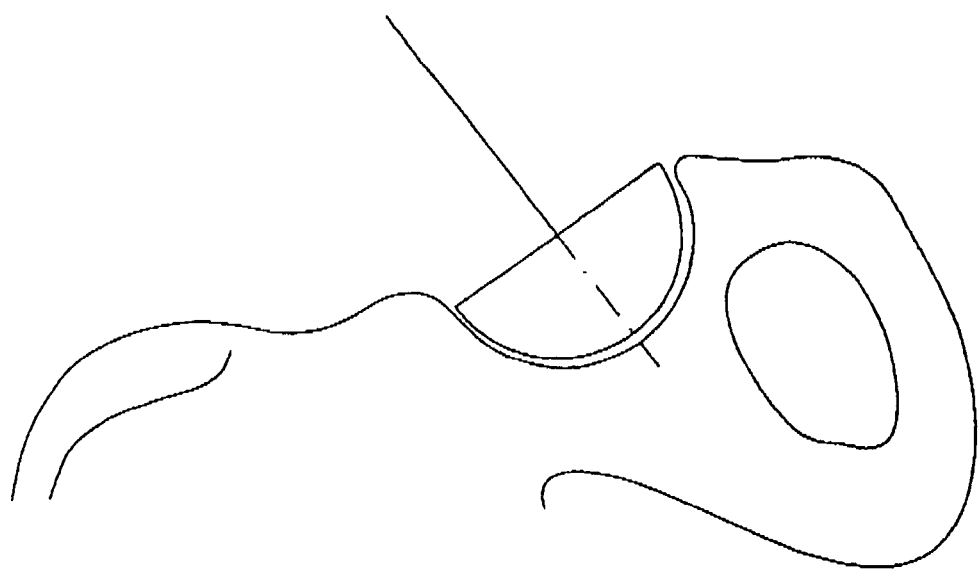
FIG. 2B is a schematic illustrating the standard acetabular reamer when the reamer is not aligned with the axis of the acetabulum.
Figure 27B:
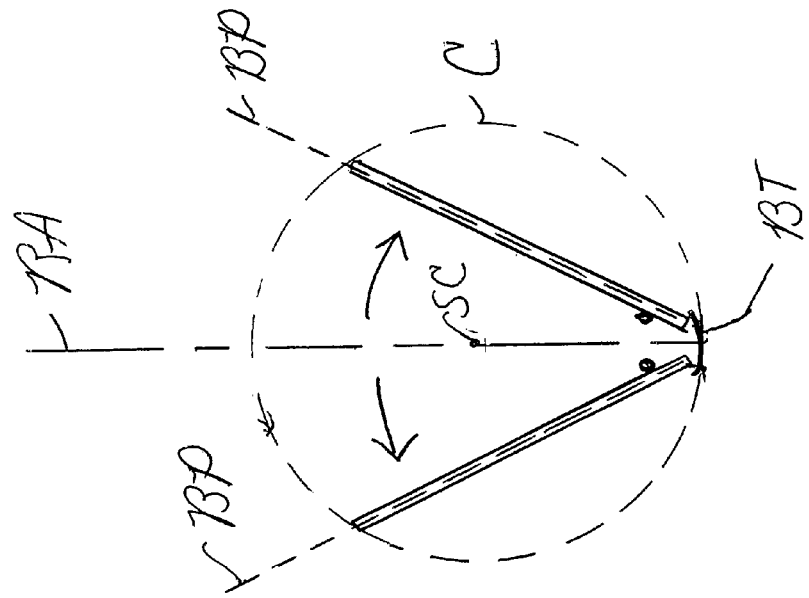
FIG. 27B is a schematic side cross-sectional view of the reamer head of FIG. 27B (same size/diameter blades) in a fully-expanded condition, again showing in dashed lines the larger effective cutting diameter/sphere of the head.
Figure 27A:
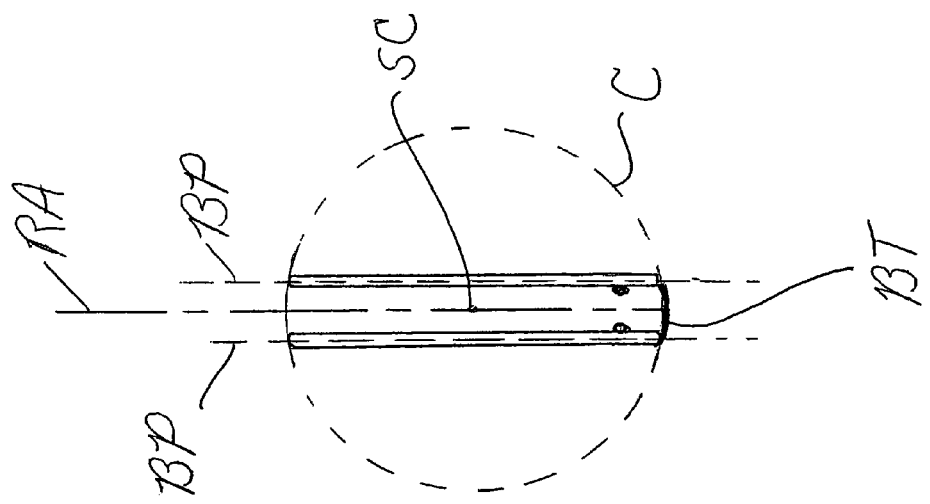
FIG. 27A is a schematic side cross-sectional view of a fully-contracted reamer head of the type of FIGS. 19-26C, showing the effective cutting diameter/sphere of the head in dashed lines.
Figure 28A:
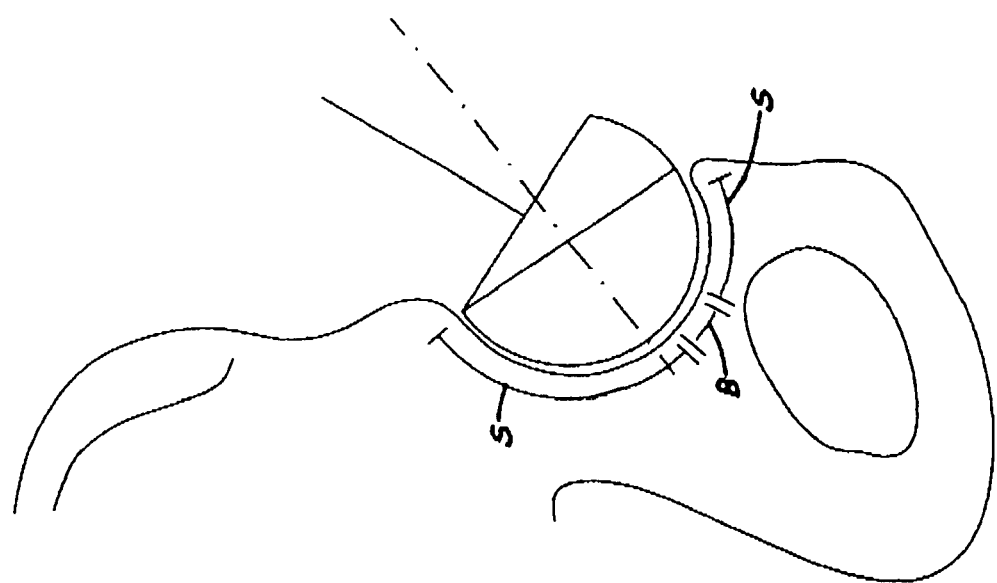
FIG. 28A is a schematic illustrating a generalized embodiment of the invented acetabular reamer of FIGS. 19-27B when the reamer is aligned with the axis of the acetabulum.
Figure 28B:
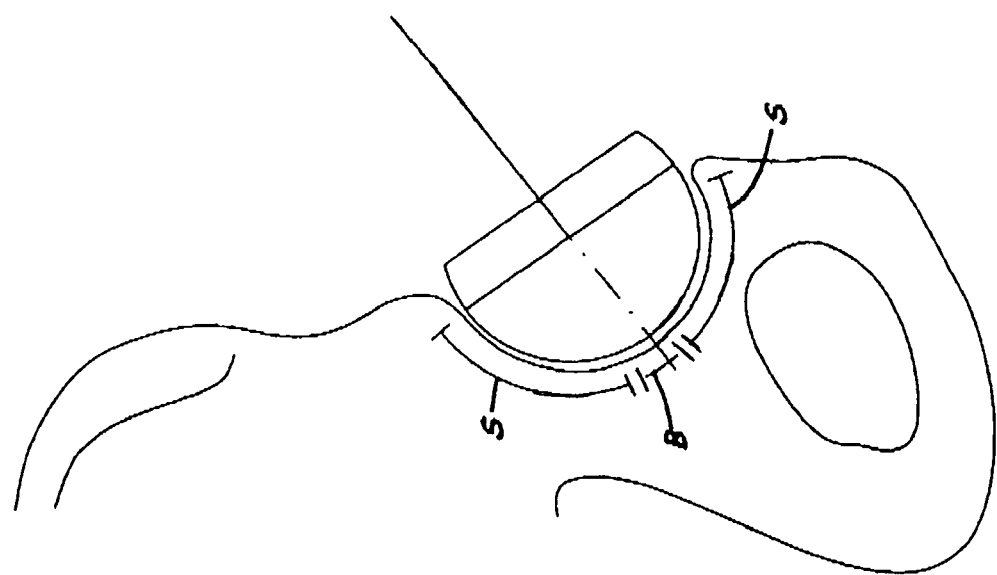
FIG. 28B is a schematic illustrating the generalized embodiment of the invented acetabular reamer of FIGS. 19-27B when the reamer is not aligned with the axis of the acetabulum.
Figure 29A:
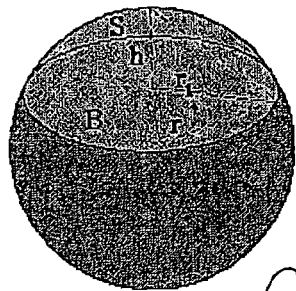
FIGS. 29A and B illustrate a spherical cap and a spherical segment, respectively, which are representations according to conventional geometry terminology. Many embodiments of the expandable blades used in embodiments of the invention may therefore be called thin segments, which, upon rotation, from a cutting sphere or a cutting sphere with a spherical cap removed (due to space being allocated for the rotational system/shaft).
Figure 29B:
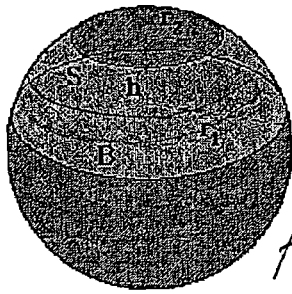
Figures 30A, 30B:
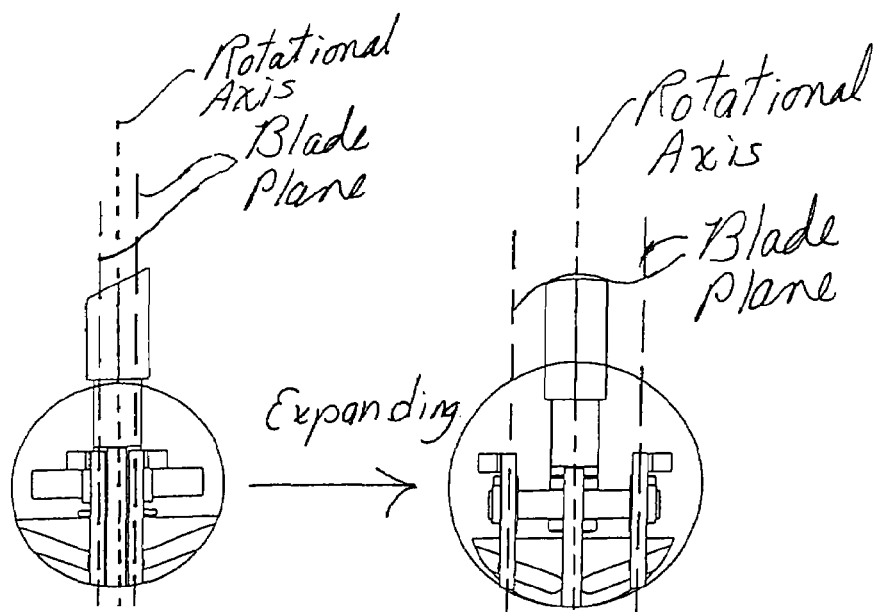
FIGS. 30A and 30B illustrate what may be called herein the "plane" of a cutting segment.

FIGS. 1A and B, and 2A and B illustrate prior art surgical techniques for hip arthroplasty. FIGS. 3-15C illustrate one embodiment of the invented reaming device and pieces-parts thereof. FIGS. 16A-E, and 17A and B schematically illustrate the preferred expansion structure and methods of the embodiment of FIGS. 3-15C, and FIGS. 18A and 18B schematically illustrate an embodiment such as that is FIGS. 3-15C in use reaming the acetabulum. FIGS. 19-26C illustrate an alternative embodiment, which has additional benefits because of its simplicity of manufacture and use, and FIGS. 27A and 27B schematically illustrate expansion of the embodiment of FIGS. 19-26C. FIGS. 28A and 28B schematically illustrate an embodiment such as that is FIGS. 19-26C in use reaming the acetabulum. FIGS. 29A and 29B illustrate the geometry of a spherical cap and spherical segment, and FIGS. 30A and 30B (and also FIGS. 27A and 27B) illustrate what may be called herein the "plane" of the cutting segment, or "blade plane."

In general, the preferred reaming device may be described as an elongated tool having a reamer head at one end and a bit or other connection or handle for receiving power at the opposing second end. The reaming device has expandable blades that may be actuated from at or near the second end of the device so that the surgeon may do so while the reamer head is inside the patient. The expansion actuation may be done by a gear system that transmits rotation of a knob or other control member near the second end of the device to rotation of an elongated member that is preferably coaxial with the central axis of the device and that extends down to the reamer head. In the embodiment of FIGS. 3-15C, said elongated member operates a worm gear assembly in or near the reamer head that transmits rotation of the elongated member to rotation of at least one worm at 90 degrees to the central axis of the device. This rotation, at 90 degrees to the central axis of the device, can be used to move the expandable blades in and out in a direction transverse to the central axis.

Preferably, multiple cutting blades are provided, wherein at least one has a cutting edge extending greater than 180 degrees, or wherein said multiple cutting blades have a group of (multiple) cutting edges that together total greater than 180 degrees. Said cutting edge is, or said group of cutting edges totals, preferably 200-270 degrees, or more preferably 220-250 degrees. Alternatively, a combination of two or more blades may have cutting edges that, when the reamer head is rotated 360 degrees, together are capable of cutting greater than a hemisphere, preferably 200-270 degrees, or more preferably 220-250 degrees. This way, no matter what the orientation of the reamer head in the acetabulum, the reamer head can cut approximately a hemisphere to receive the hemispherical prosthetic socket. See FIGS. 18A and 18B.

The expansion of the reamer head is done with preferred structure and methods that provide extremely accurate reaming of various hemispherical diameters. At least one of the preferred moveable cutting blades serves as a segment of the "cutting sphere" (more precisely, a segment of a sphere with a spherical cap removed). See FIGS. 29A and B. When the segment is moved outward in a direction that is non-parallel to its plane, the segment becomes a segment of a larger sphere, and, hence, "expands" the sphere, or, in other words, "expands" the effective size of the sphere created by rotating the reamer head. In many embodiments of the invention, the cutting blades may be said to move transversely or generally transversely relative to the axis of rotation of the reaming head and/or transversely or generally transversely (perpendicularly or generally perpendicularly) to its own plane, wherein "its own plane" is illustrated in FIGS. 27A and B and 30A and B as the central plane through the typically plate-like segment/blade. While the blades need not be perfectly plate-shaped or have perfectly planar front or back surfaces, and the blades may have various thicknesses, the blades will tend to be generally plate-like and, hence, be describable as having a "central plane" or "blade plane." Upon moving in a direction non-parallel to its plane, the same segment (and hence, the same blade) becomes a segment of a larger cutting sphere. Therefore, by moving at least one "cutting segment" outward, the effective spherical diameter of the rotating reamer head increases so that the diameter of the reamed surface also increases.

In the embodiment of FIGS. 3-15C, two of these blades acting as "cutting segments" are provided, parallel to each other and moveable outward on opposite sides of the head. The preferred segments each have a leading cutting edge(s) that total greater than 180 degrees on a single radius (being portions of a circumference). This provides a set of two greater-than-180-degree blade cutting edges, following the same rotational path, but on opposite sides of the head, for providing a balanced head and for increasing the total length of cutting edge. The circular edge of each of the segments is mainly for reaming the "sides" S of the acetabulum (FIGS. 18A and B), especially as the segments are moved out from the central axis of the reamer head, because, in effect, they rotate around the central axis of the head a distance from the axis.

Figure 18B:
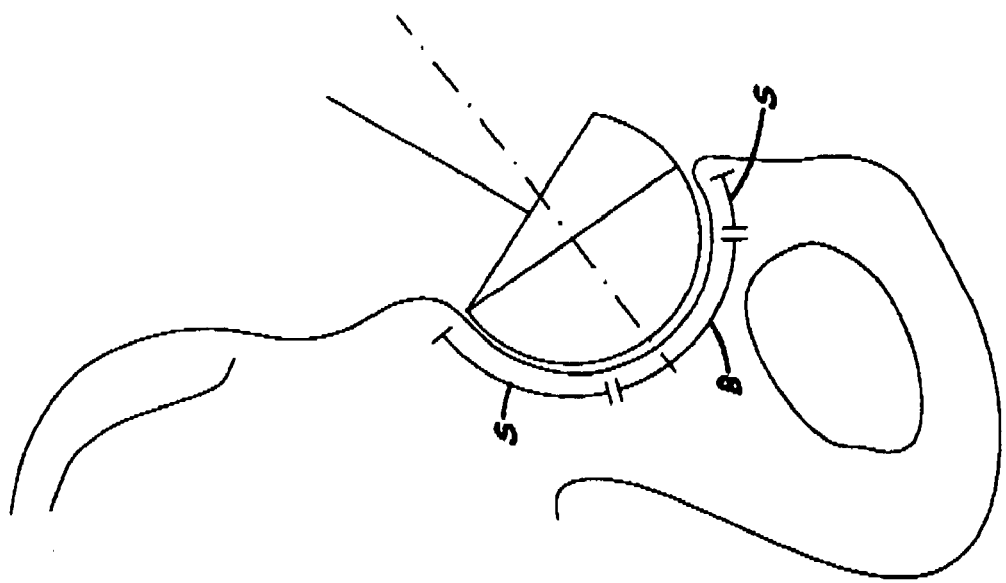
FIG. 18B is a schematic illustrating a generalized embodiment of the invented acetabular reamer during use when the reamer is not aligned with the axis of the acetabulum.
Figure 18A:
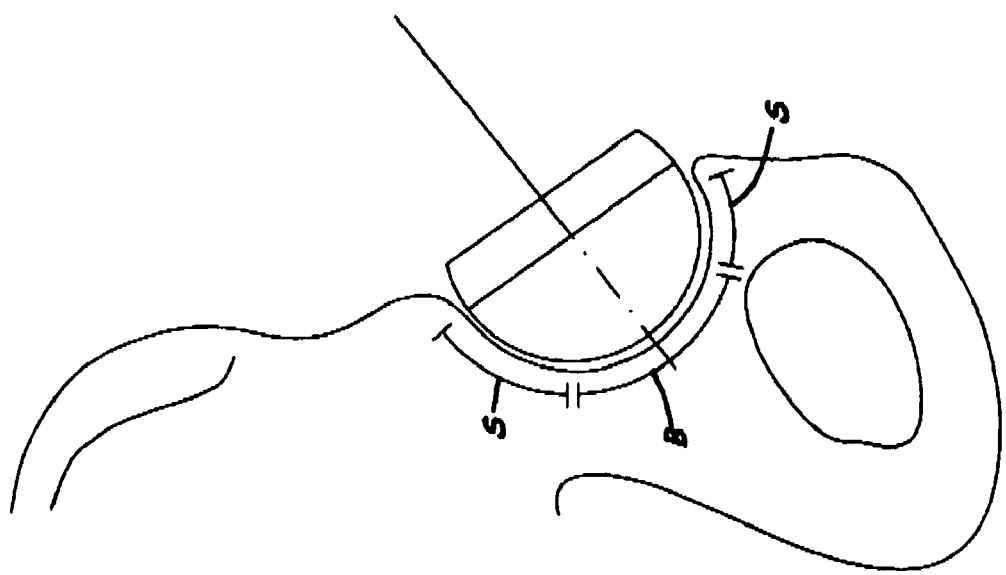
FIG. 18A is a schematic illustrating a generalized embodiment of the invented acetabular reamer during use when the reamer is aligned with the axis of the acetabulum.

The circular edge of an additional blade extending parallel to and through the central axis is used for cutting the "bottom" B of the acetabulum in FIGS. 18A and B, that is, the curved bottom surface of the acetabulum (starting from the center axis of the head and extending out a distance generally equal to said distance of the cutting segments from the axis). In the preferred reamer head of FIGS. 3-15C, two blades are provided that extend parallel to and through the axis of rotation and that are preferably perpendicular to each other. One or both of these blades, or portions of one or both of these blades may be sharpened or otherwise shaped for cutting/reaming the bottom B. One or both of these blades should have edges or portions or their edges that together or individually, upon a revolution of the reamer head, ream the bottom B in the area from the central axis of the tool to the radial location of the cutting segments. One or both may have a portion that, instead of cutting, mainly moves bone material out of the way after it has been cut from the acetabulum by the other blades. See FIGS. 18A and 18B, illustrating the "sides" S portions and "bottom" B portion of the acetabulum, wherein these portions change depending on the orientation of the device in the acetabulum. Also, these portions will change as the reamer head is expanded (not shown in FIGS. 18A and B). The portion of the acetabulum being reamed by the blade(s) extending through the central axis will increase, while the portion being reamed by the cutting segments will decrease.

The cutting segment structure and method of expanding the reamer head may be better understood by viewing FIGS. 16A-E, which show progressive stages of expansion of blades such as those in FIGS. 3-15C, and FIGS. 17A and B, in which the expansion is exaggerated, compared to that normally desired in a surgical reaming device, for the sake of clarity. In FIGS. 17A and B, the moveable blades are called-out as 25' and 35', the central blade is called-out as 30', and the transverse blade is called-out as 20'.

Alternatively, blades may move, in other ways and in direction(s) that are non-parallel to their planes. For example, blades may move perpendicularly or generally perpendicularly to their respective planes by pivoting in directions that are not parallel to their respective planes. Also, alternative actuation systems may be used for expanding the blades. One such embodiment illustrating pivoting blades and an alternative actuation system is illustrated in FIGS. 19-26C, with its operation illustrated schematically in FIGS. 27A, B, and 28A and B.

For example, a member on the outside of the rotating shaft system may force at least one pivot arm down to expand at least one expandable blade. In the embodiment of FIGS. 19-26C, preferably a first and second of said pivot arms are linked to the sleeve member at their upper ends, and are linked to first and second expandable blades, respectively, at their lower ends. Upon pushing the sleeve down to push the upper ends of the pivot arms down parallel to the rotational axis of the reamer, the pivot arms expand and the expandable blades expand. In reverse, pulling upwards on the sleeve will raise the upper ends of the pivot arms, contract the lower ends of the pivot arms and contract the expandable blades.

Each blade is generally a plate having a blade plane, and each blade has a pivot axle parallel to its plane and near its bottom edge. As previously discussed herein, the blades need not be perfectly plate-shaped or have perfectly planar front or back surfaces, and the blades may have various thicknesses, but the blades will tend to be generally plate-like and, hence, be describable as having a "central plane" or "blade plane." Each blade pivots on its pivot axle so that the blade above the pivot axle swings outward away from the rotational axis of the reamer and the blade below the pivot axle swings inward toward the rotational axis. See FIGS. 27A and B for schematic representations. Because the pivot axles are so near the bottom edges of their respective blades and near the bottom of the reamer, the blades may be described as expanding by pivoting substantially outward in a direction perpendicular to their planes. Preferably, the pivot axles are located on the blade in the range of ¼-⅙ (and more preferably about ⅕) of the way up the blade from the blade bottom edge, so that from ¾ to ⅚ of the blade pivots outward away from the rotational axis and only ¼-⅙ of the blade pivots inward toward the rotational axis. Thus, it may be said that a substantial portion of the blade pivots outwards away from the rotational axis.

Said at least one (and preferably two) expandable blade(s) has(have) a cutting edge extending greater than 180 degrees, or a group of cutting edges that together total greater than 180 degrees. Said cutting edge is, or said group of cutting edges totals, preferably 200-325 degrees, or more preferably 250-330 degrees, so that, when the blades are pivoted outwards and their top edges are, in effect lowered, most of the top edges are still capable of reaming and greater than a hemisphere may be reamed. Alternatively, a combination of two or more blades may have cutting edges that, when the reamer head is rotated 360 degrees, together are capable of cutting greater than a hemisphere, preferably 200-325 degrees, or more preferably 250-330 degrees. This way, no matter what the orientation of the reamer head in the acetabulum, the reamer head can cut approximately a hemisphere to receive the hemispherical prosthetic socket. See FIGS. 28A and 28B. As in the case of the description of the embodiment of FIGS. 3-17B, when the phrase "no matter what the orientation of the reamer head in the acetabulum" is used, it is understood that this refers to the orientations that would typically result from hip arthroplasty, including those resulting from both standard "large incision" arthroplasty and "small incision" MIS arthroplasty.

The expansion of the reamer head of FIGS. 19-26C is done with preferred structure and methods that provide extremely accurate reaming of various hemispherical diameters. At least one, and preferably two, of the preferred moveable cutting blades serves as a segment of the "cutting sphere" (more precisely, a segment of a sphere with a spherical cap removed). When the segment is moved outward by pivoting out transversely to the plane of the segment/blade, that same segment, in effect, becomes a segment of a larger cutting sphere. Therefore, as discussed above, moving at least one "cutting segment" outward, the effective spherical diameter of the rotating reamer head increases so that the diameter of the reamed surface also increases, and a larger cutting sphere is created that is extremely accurate.

In the embodiment of FIGS. 19-26C, two of these blades acting as "cutting segments" are provided, at first generally parallel to each other (when completely contracted), and moveable outward on opposite sides of the head, by pivoting away from each other at their top ends. The preferred segments each have a leading cutting edge that totals greater than 180 degrees on a single radius (being a portion/portions of a circumference). This provides a set of two greater-than-180-degree cutting edges, following the same rotational path, but on opposite sides of the head, for providing a balanced head and for increasing the total length of cutting edge. The circular edge of each of the segments is mainly for reaming the "sides" S of the acetabulum (See FIGS. 28A and B), because they rotate around the central axis of the head a distance from the axis.

The circular edge of an additional blade extending parallel to and through the central axis is also used for cutting/reaming. The preferred reamer head of FIGS. 19-26*c* is made so that the transverse blade diameter is the diameter of the sphere of which the two expandable blades are segments when in the fully-contracted condition. Therefore, when the head is fully-contracted, the transverse blade and also the expandable blades are all cutting/reaming. Then, as the head is expanded, the expandable blades "take over" as they define the diameter of the cutting sphere, rather than the transverse blade. Even when the head is expanding/expanded, however, a portion of the transverse blade will continue to cut/ream and, hence define a portion of the concave surface being formed by the device, that is, the "bottom" B of the acetabulum. See FIGS. 27A, 27B, 28A, and 28B. With this embodiment, bottom B is a very small curved bottom surface portion of the acetabulum, as it is cut by the transverse blade portion that is between the rotational axis and the portions of the cutting segment bottom edges that are on the "cutting sphere surface" and so are positioned properly to ream. Because the bottom edges of the cutting segments are so close to the central axis in this embodiment, whether contracted or expanded, said distance is very short. Therefore, the reaming sphere "surface" is created by a very small portion of the rotating transverse blade edge and the majority of the rotating cutting segment edges, and, hence, is nearly a perfect sphere. Of note here is that the bottom edges of the cutting segments move closer to the center axis as the blades are expanded, and so, while the bottom extremity of the blades moves slightly in and up relative to the central axis, the portions of the blade that are on the cutting sphere and, therefore, are reaming, are still just above the bottom extremity and are close to the central axis. See FIGS. 27A and B, and FIGS. 28A and B.

Figure 6:
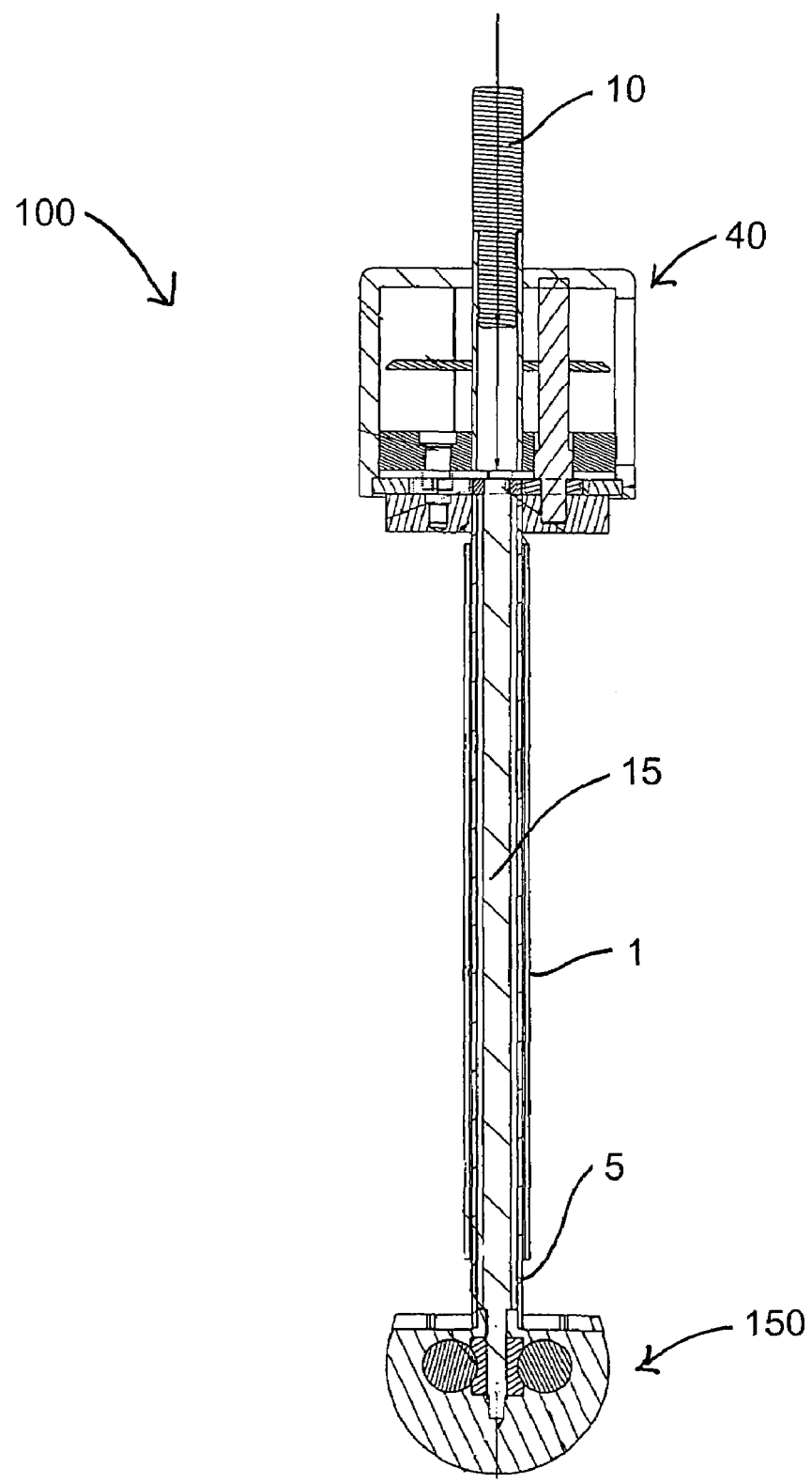
FIG. 6 is an enlarged version of the right side cross-sectional view of FIG. 5A.

The cutting segment structure and method of expanding the reamer head of FIGS. 19-26C may be better understood by viewing FIGS. 27A and 27B, which show the fully contracted condition and an expanded condition of blades such as those in FIGS. 19-26C. In FIG. 27A, 6 centimeter diameter blades B create an approximately 6.2 centimeter diameter cutting sphere C upon rotation of the blades. In FIG. 27B, the same 6 centimeter diameter blades are expanded by pivoting, forming approximately a 7.3 centimeter diameter cutting sphere C. The cutting spheres C are shown in FIGS. 27A and 27B as two dimensional, for ease of illustration, but it is understood that the cutting spheres are formed by rotation of the reaming head and, hence, are three dimensional (spheres rather than circles). Blade planes BP, rotational axis RA, sphere center SC, and the bottom portion of the transverse blade BT are also shown in FIGS. 27A and 27B.

Figure 3:
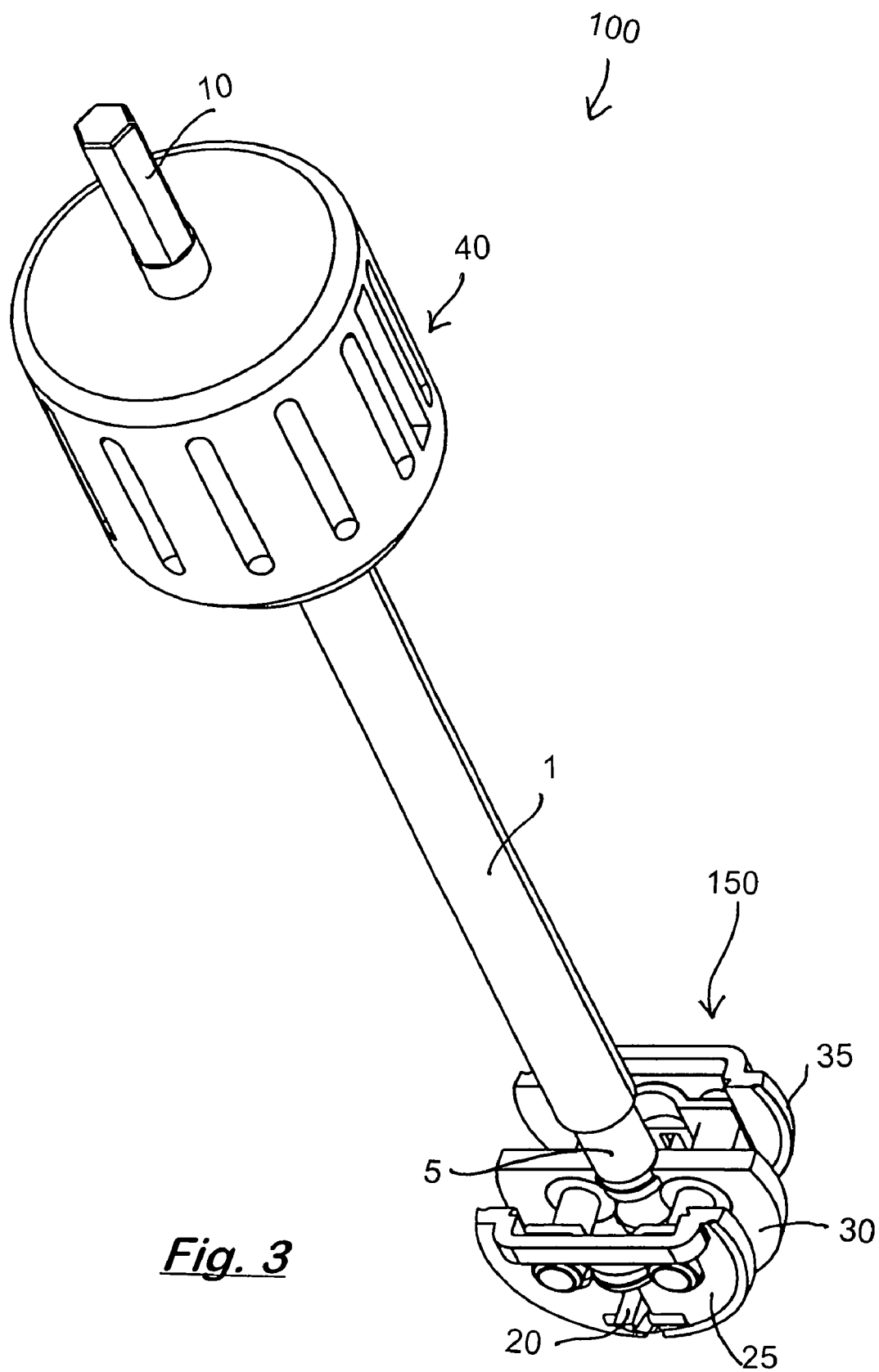
FIG. 3 is a perspective view of one embodiment of the invented reaming device.

Referring specifically to FIGS. 3-15C:

As shown in FIG. 3, the preferred embodiment of the invented expandable reamer 100 comprises a rotating shaft 5; a drill bit 10 on one end of the rotating shaft 5 for cooperating with a surgical drill; an expansion control rod 15 inside said rotating shaft 5; a reamer head 150 comprising three cutting blades 25, 30, 35 and a transverse guide blade 20 operationally connected to the rotating shaft 5; a knob 40 for actuating a gearing system and the expansion control rod 15 to expand radially at least one and preferably two of the cutting blades to be the "cutting segments" described above. Preferably, a portion of the rotating shaft 5, with the expansion control rod 15 inside the shaft, is contained within a handle sleeve 1 that floats freely on the outside of the main shaft 5 for being grasped by the surgeon.

As shown in FIGS. 5A, 5B, 6, and 7 to best advantage, the drill bit 10 is rigidly connected to the rotating shaft 5, and the rotating shaft is preferably rigidly connected to the central cutting blade 30, wherein "connected" may imply a direct connection, or an indirect connection including intermediate or intervening connectors. For example, as illustrated in FIGS. 5A, 5B, 6, and 7, the drill bit 10 is rigidly connected to tubular shaft portion 5', which is rigidly connected to top plate 45. Top plate 45, as is further discussed later in this Description, is rigidly connected to bottom plate 42 (for example, by screws), which is rigidly connected to the main shaft 5. Thus, drill bit 10, tubular shaft portion 5', top plate 45, bottom plate 42, and main shaft 5 collectively may be called the rotational shaft system of this embodiment. Main shaft 5 is rigidly connected to the guide blade 20, which is preferably fixed to and perpendicular to the central blade 30, and the expandable blades 25, 35 ride on worms mounted in the central blade 30 and are guided by sloped channels 22, 24 in the guide blade 20.

In operation, a power unit (may be a conventional, hand-held, surgical reaming power unit, for example, not shown) connected to the drill bit 10 serves to rotate the entire reaming device 100, including the expansion actuation system (knob 40, planetary gear system 41, control 15, and worm gear system) but with the exception of the floating sleeve 1. The sleeve 1 is gripped in the surgeon's hand for stabilizing and guiding the reaming device 100 but does not interfere with rotation of the device 100. Typically, the surgeon will grasp the power unit in one hand and the sleeve 1 in the over. Rotating the bit 10 rotates the shaft 5, which rotates the entire reamer head 150, with power being transmitted from the power unit to the reaming head via the rotational shaft system (drill bit 10, tubular shaft portion 5', top plate 45, bottom plate 42, and main shaft 5). When expansion is desired, rotation is stopped, and the expansion actuation is operated relative to the rotational shaft system to expand the blades, all without removing the reaming head from the patient. With one hand on the power unit, the surgeon may rotate the knob 40 with his other hand to actuate blade expansion. The surgeon may then return to reaming by returning his non-power-unit-grasping hand to the sleeve for guiding and stabilizing the reaming device 100.

Figure 4C:
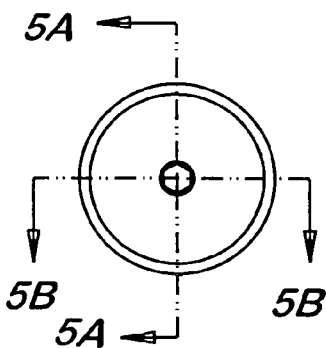
FIG. 4C is a top view of the embodiment of FIG. 4A, used to show the direction of cross-sectional views for FIGS. 5A and 5B.
Figure 4A:
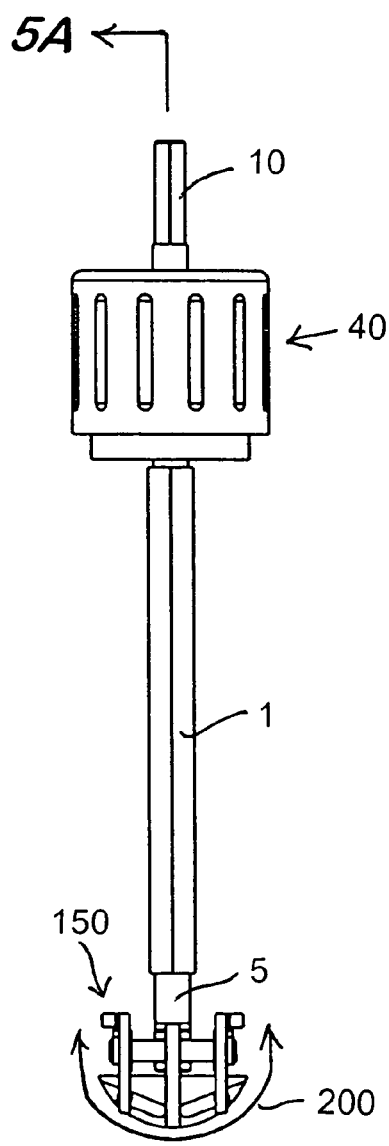
FIG. 4A is a front view of the embodiment shown in FIG. 3, with the rear view being the same due to the preferred symmetry of the device.
Figure 4B:
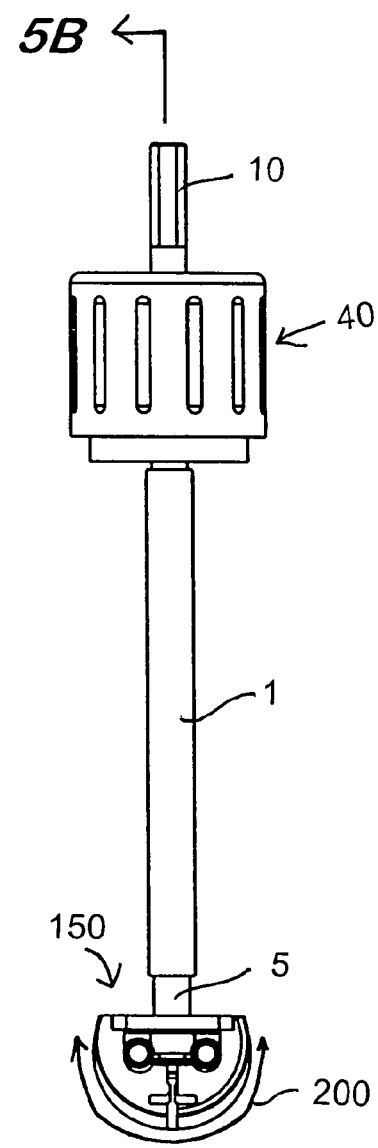
FIG. 4B is a right side view of the embodiment shown in FIGS. 3-4A, with the left view being the same due to the preferred symmetry of the device.
Figure 5A:
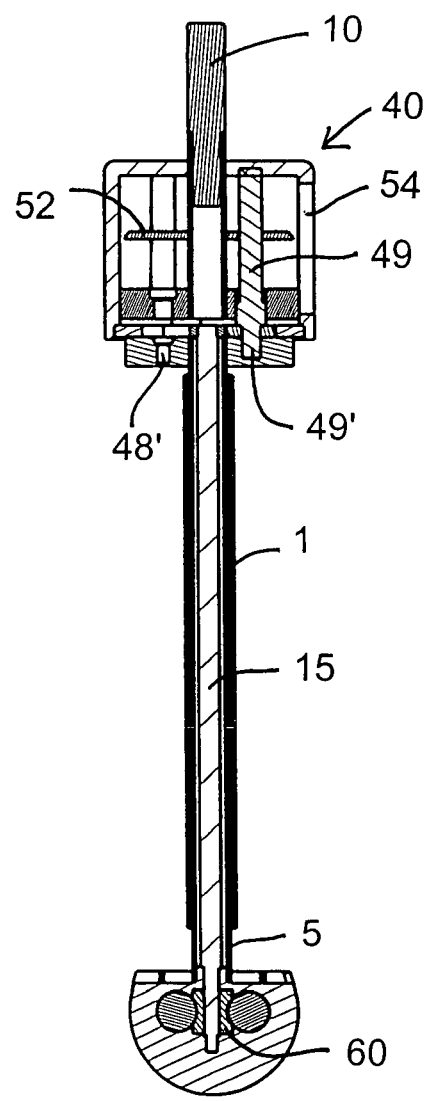
FIG. 5A is a right side cross-sectional view of the embodiment shown in FIGS. 3-4B, viewed along the line 5A-5A in FIGS. 4A and 4C.
Figure 5B:
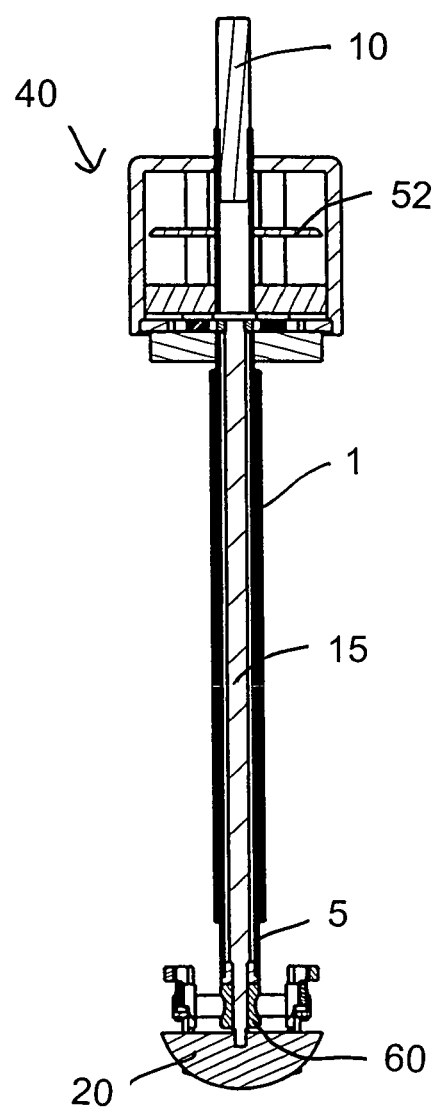
FIG. 5B is a rear cross-sectional view of the embodiment shown in FIGS. 3-5A, viewed along the line 5B-5B in FIGS. 4B and 4C.

As illustrated to best advantage in FIGS. 4A and 4B, each of the three parallel cutting blades 25, 30, 35 has an outer circumference curving on its respective single radius and is greater than 180 degrees (preferably 200-270 degrees, and more preferably 220-250 degrees), so that, when the reamer head is rotated, the cutting blades 25, 30, 35 are capable of cutting/reaming a portion of a sphere 200 that is 180 degrees or greater than 180 degrees. More precisely, in the preferred application, the sphere portion 200 is capable of cutting/reaming a hemisphere in the acetabulum even when off-axis relative to the acetabulum.

As discussed above, knob 40 may be rotated relative to the rotational shaft system in order to actuate the gearing system that expands cutting blades 25, 35. Knob 40 is typically operated only when the user has stopped rotation of the shaft 5 and the reamer head 150. The knob 40 is preferably manually operated, whereby, as shown in FIGS. 5A, 5B, 6 and 7, turning knob 40 relative to the rotational shaft system serves to rotate the planetary gear system housed in the interior space of the knob, which in turn rotates the control rod 15, which in turn operates the gearing system in the reaming head, as further detailed below. As shown in FIGS. 5A, 5B, 6 and 7, a top plate 45, planetary gear system 41, and an indicator disk system are housed within knob 40, with bottom portions of the planet gears rotationally supported in bottom plate 42 (see FIGS. 7, 8A-8C).

Figure 7:
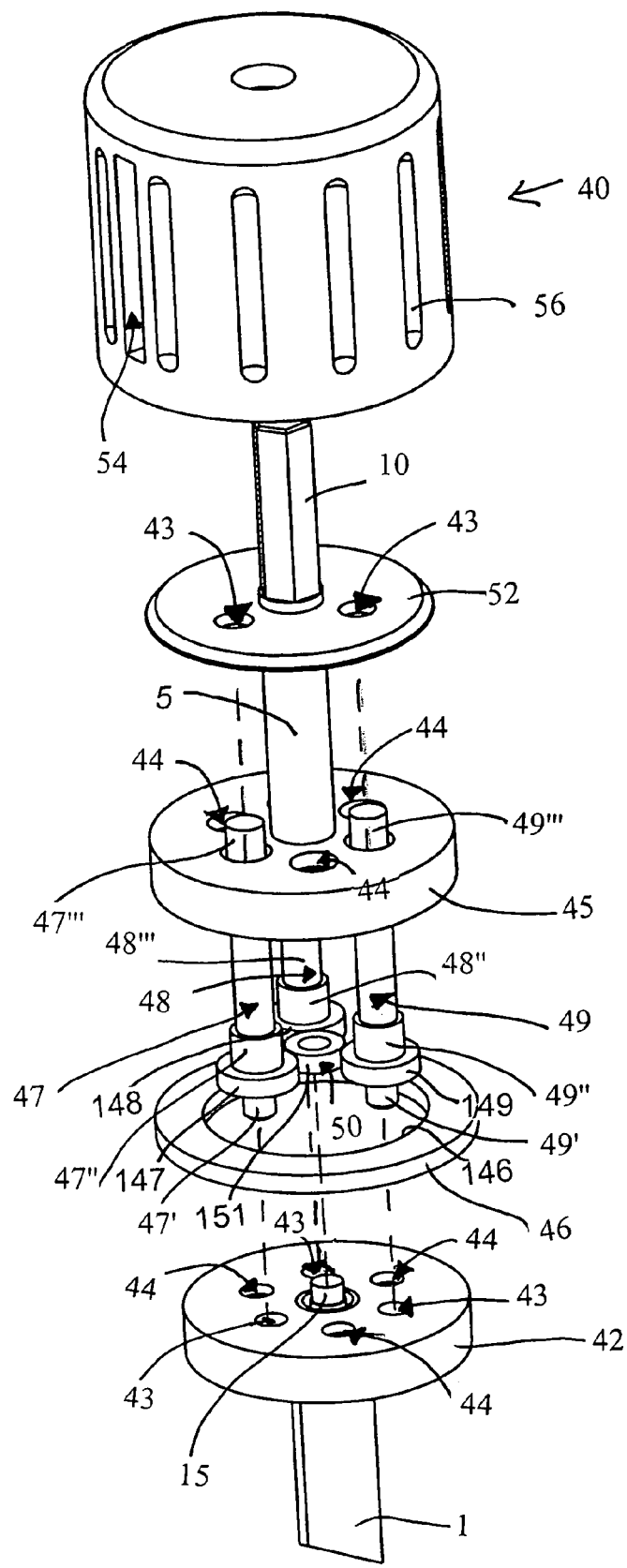
FIG. 7 is a partial exploded view of the embodiment shown in FIGS. 3-6B, featuring the planetary transmission system used for adjusting the moveable blades.
Figure 9:
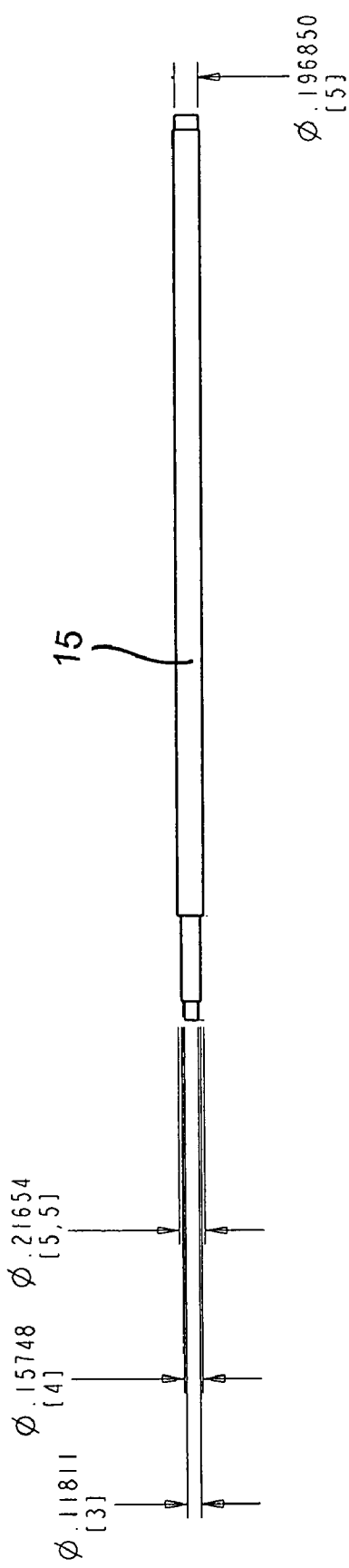
FIG. 9 is a side view of the central rod of the embodiment shown in FIGS. 3-8C.

As shown in FIG. 7, the planetary gear system 41 comprises a system of spur gears in which the toothed inner surface 146 of an outer gear ring 46 turns three inner planet gears 47, 48, and 49, which in turn drive a central sun gear 50. The outer perimeter of the gear ring 46 is rigidly attached to the bottom of the knob 40, and the sun gear 50 is rigidly connected to the expansion control rod 15 (see FIGS. 7 and 9). The three planet gears 47, 48, and 49 each comprise a bottom portion 47', 48', and 49', toothed portion 147, 148, and 149 for meshing with the toothed inner surface 146 of the ring 46 and the toothed outer surface 151 of the sun gear, a sleeve portion 47", 48", and 49", and a top portion 47''', 48''', and 49'''. In the preferred embodiment, the gear ring 46, the toothed portion 147, 148, and 149 and the sleeve portion 47", 48", and 49", and the sun gear 50 are contained between the bottom plate 42 and top plate 45.

Preferably, the bottom plate 42 and top plate 45 each contain six apertures: three apertures 43 for the planet gears 47, 48, 49 and three apertures 44 for screws to hold the bottom plate 42 and top plate 45 together. The bottom portions 47', 48', and 49' of the planet gears insert into the apertures 43 in the bottom plate 42, the top portions 47''', 48''', and 49''' extend up through the apertures in the top plate 45 and through planet gear apertures 43 in the indicator disk 52. The two plates 42 and 45 are held together by screws (not shown) which insert into the screw apertures in the top and bottom plates 45, 42. The two plates 42 and 45 are separated by the sleeve portions 47", 48", and 49" on the planet gears to allow room for the gear ring 46 and planet gears 47, 48, 49 to rotate.

In the preferred embodiment, one of the planet gears 49 is threaded on its top portion 49'''. The indicator disk 52 threadably engages the top portion 49''' while the other two planet gears 47 and 48 merely pass through the apertures 43 in the indicator disk without engaging the disk 52. The knob 40 comprises one or more viewing windows 54 for viewing the indicator disc 52.

As the knob 40 is turned, the gear ring 46 also turns, in turn rotating the planet gears 47, 48, and 49, which rotate the sun gear 50, which rotates the rod 15, in turn expanding the two outer cutting blades 25 and 35 via a worm gear system such as will be discussed below. As the planet gears 47, 48, and 49 are rotating, the preferred indicator disk 52 rides up and down on the threaded planet gear top end 49''', with how far it moves indicating how far the blades 25, 35 have expanded. There may be indicia on the knob 40 surface outside the viewing window(s) 54 to allow the surgeon to know exactly how far out the blades 25 and 35 have moved. Further, the indicating disk may be a color, such as red or another easily-visible color, to aid in seeing the indicator disk 52 through the viewing window 54. Additionally, the knob 40 may be fitted with traction bumps 56 to aid in gripping and turning the knob 40.

Figure 10D:
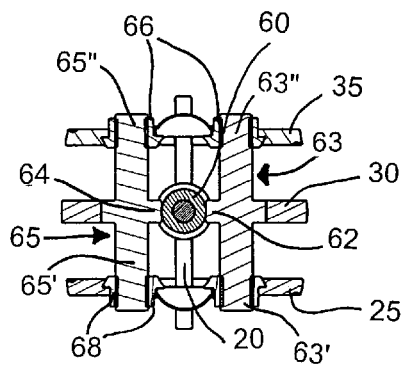
FIG. 10D is a cross-sectional top view of the head of the reamer of FIGS. 3-9, viewed along the line 10D-10D in FIG. 10A.
Figures 10A, 10B, 10C:
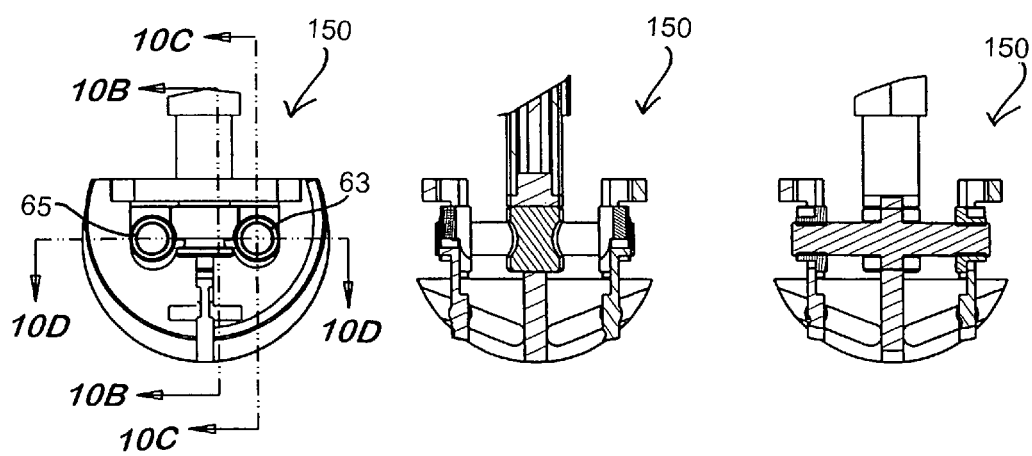
FIG. 10A is a side view of the head of the reamer of the embodiment shown in FIGS. 3-9.
FIG. 10B is a cross-sectional view of the head of the reamer of FIGS. 3-9, viewed along the line 10B-10B in FIG. 10A.
FIG. 10C is a cross-sectional view of the head of the reamer of FIGS. 3-9, viewed along the line 10C-10C in FIG. 10A.
Figure 11A:
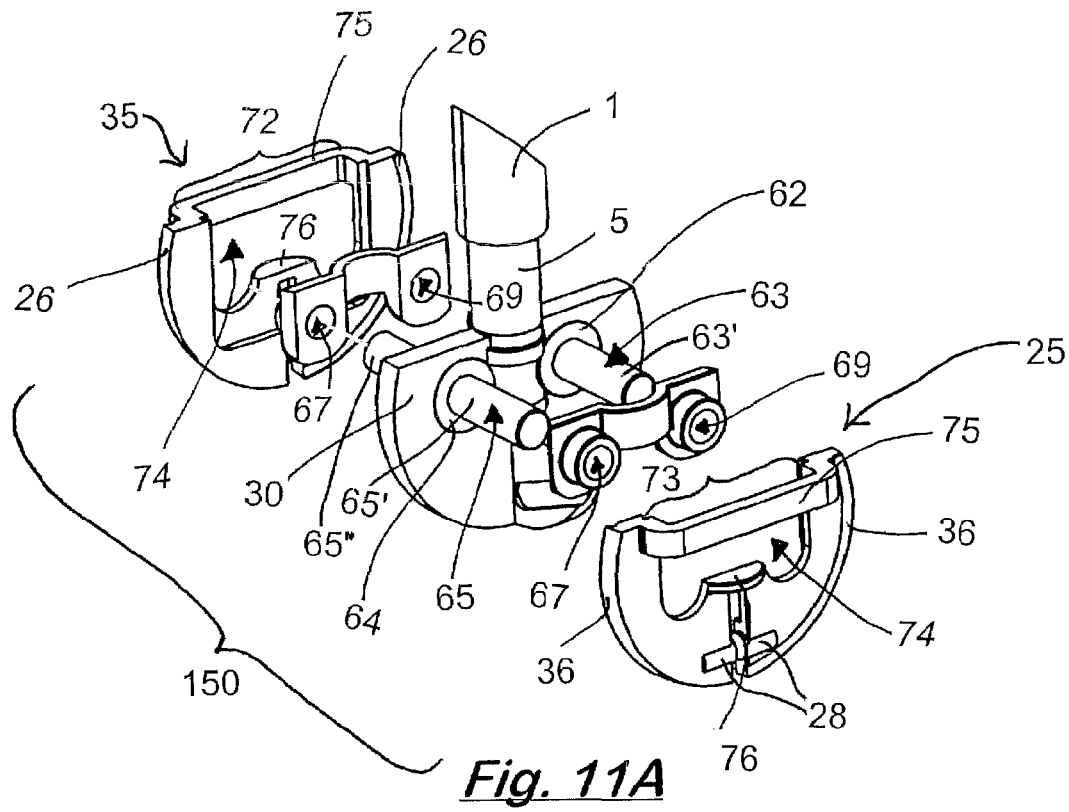
FIG. 11A is an exploded view of the head of the reamer of the embodiment shown in FIGS. 3-10D.

The expansion control rod or "center rod" 15 preferably extends down from the sun gear 50 through the shaft 5 and is coaxial and fixed with the center of a worm gear 60 (see FIGS. 5, 6A-6B, 10A-D, and 11A). Preferably, the worm gear 60 is right hand threaded to mesh with two center toothed portions 62, 64 on two cooperating worms 63, 65. The two center portions 62, 64 of the worms 63, 65 are rotatably mounted in, or otherwise extending through, the central blade 30. Preferably, worm 63 has left hand threads on one of its ends 63' and right hand threads 63" on the other of its ends (FIGS. 10D and 11A). The threads on the two ends of worm 65 are oriented to be opposite those of worm 63, so that end 65' of worm 65 has right hand threads, and end 65" of worm 65 has left hand threads.

Figure 11B:
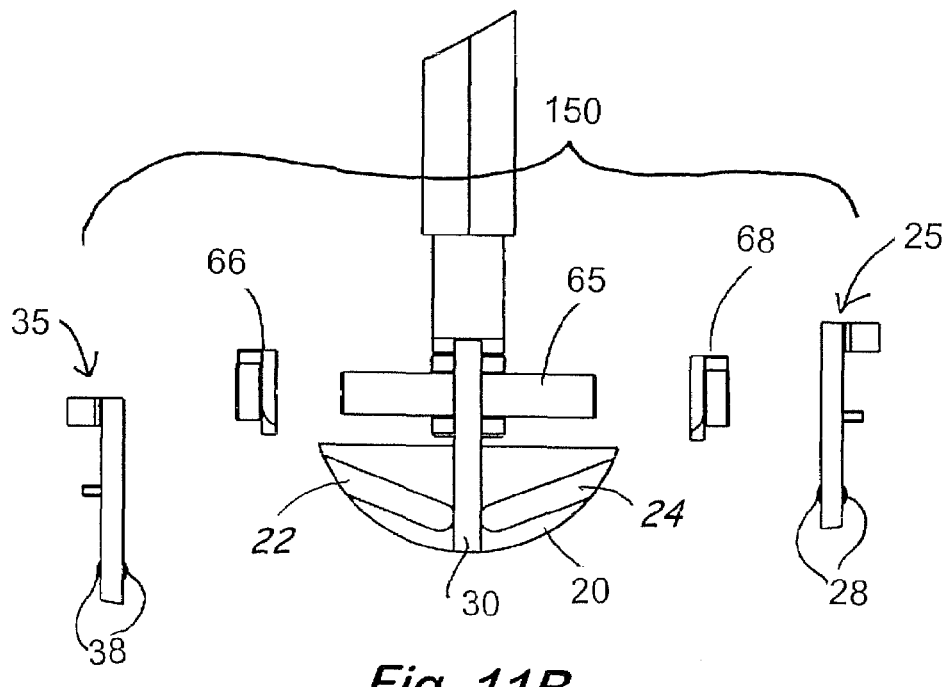
FIG. 11B is a front exploded view of the head of FIG. 11A.
Figure 12B:
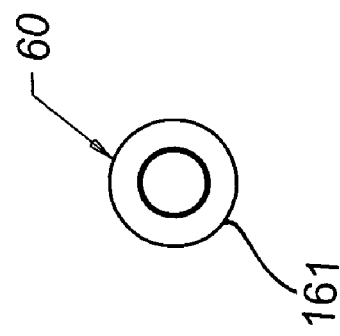
FIG. 12B is an end view of a worm gear of the embodiment shown in FIGS. 3-12A, wherein the worm gear is drawn without its teeth.
Figure 12A:
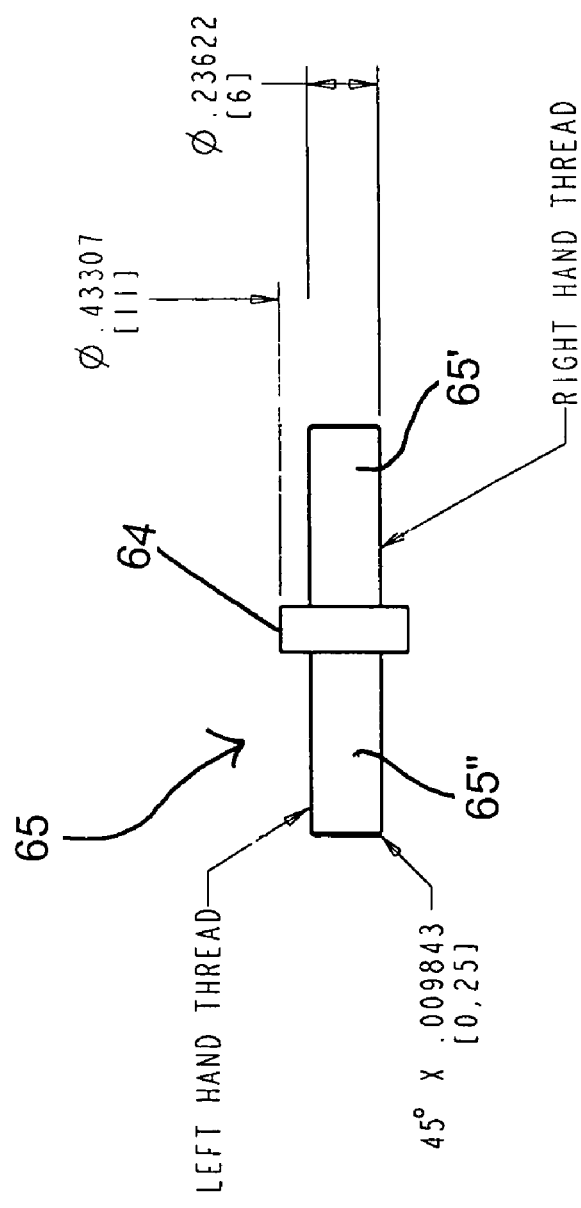
FIG. 12A is a front view of the worm of the embodiment shown in FIGS. 3-11B, wherein the worm is drawn without its teeth and threads.
Figure 13A:
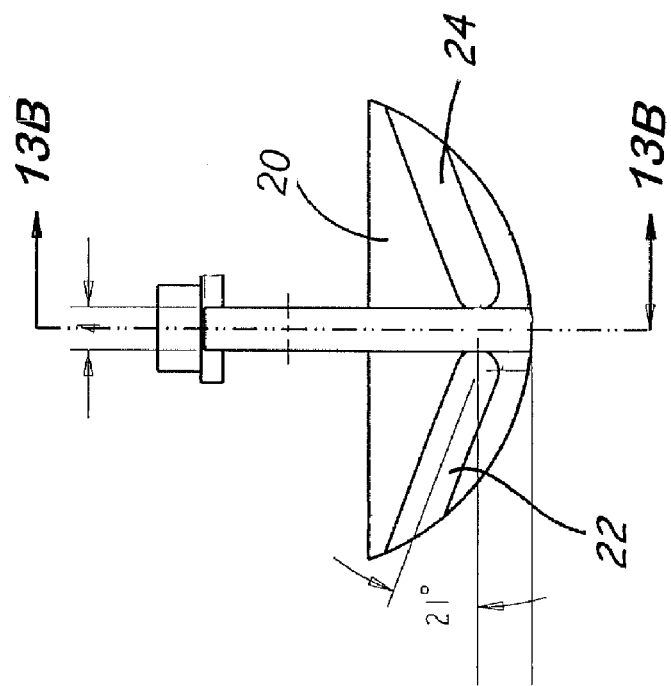
FIG. 13A is a front view of the central blade and guide blade combination of the embodiment shown in FIGS. 3-13A.
Figure 13B:
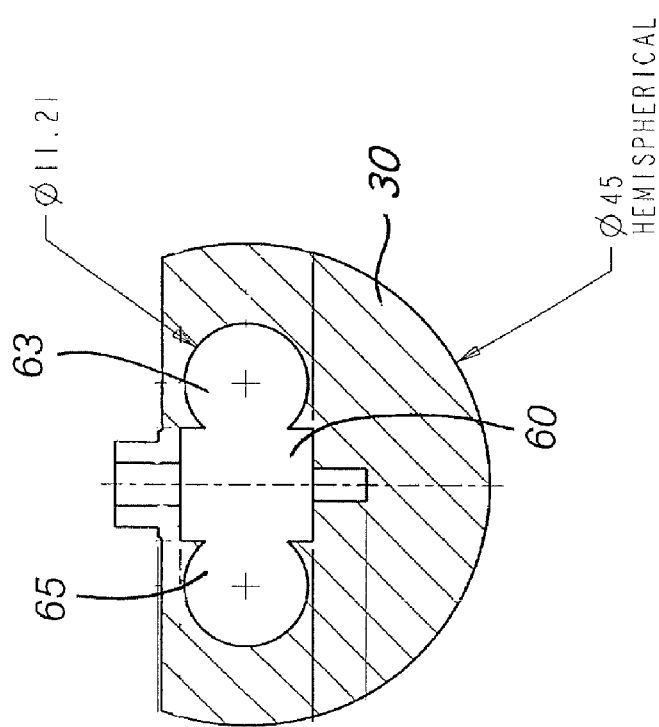
FIG. 13B is a cross-sectional view of the central blade of the embodiment shown in FIGS. 3-12B, viewed along the line 13B-13B in FIG. 13A.
Figure 14:
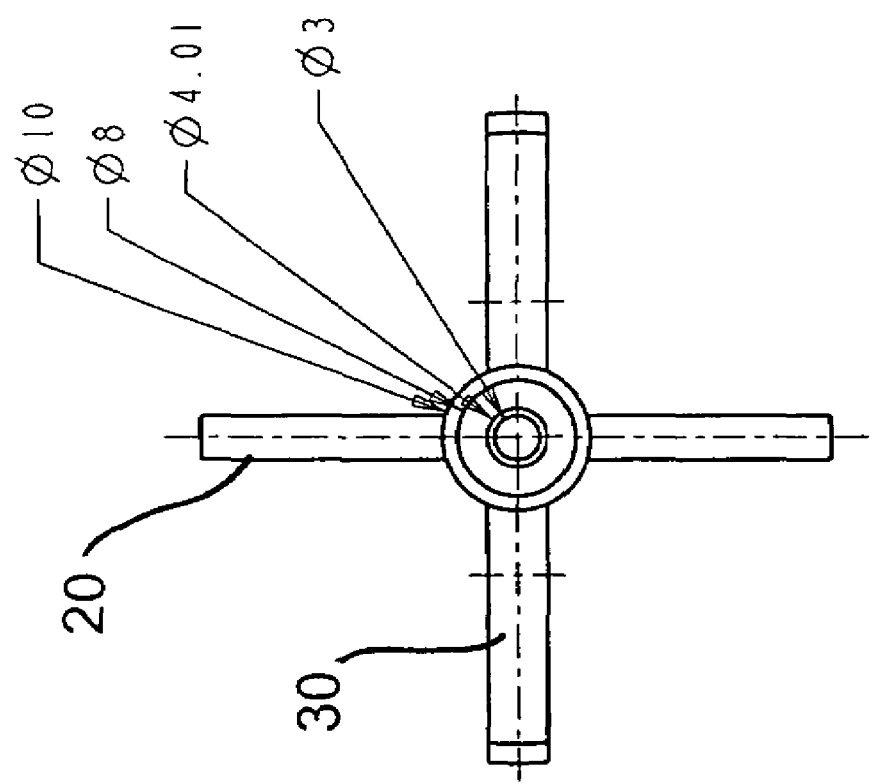
FIG. 14 is a top view of the central blade and guide blade of the FIG. 13A.
Figure 15C:
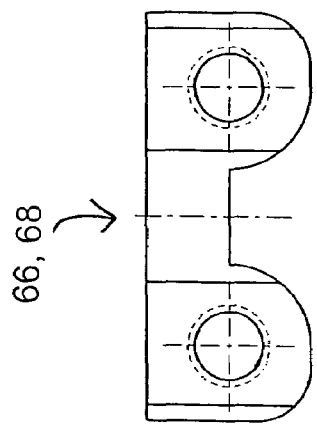
FIG. 15C is a second (opposing) side view of the gear plate of FIGS. 15A and B.
Figure 15D:
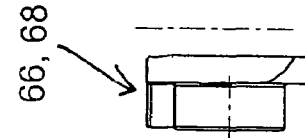
FIG. 15D is an end view of the gear plate of FIGS. 15A-C.
Figure 15B:
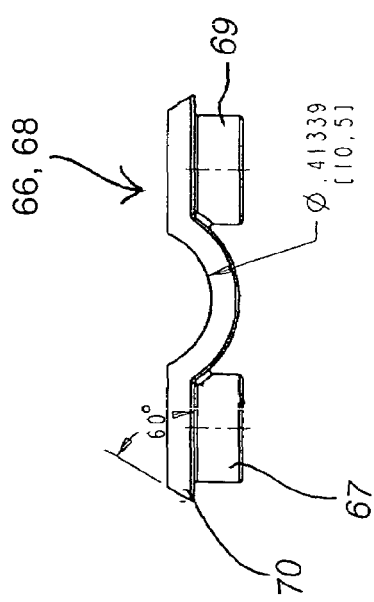
FIG. 15B is a top view of the gear plate of FIG. 15A.
Figure 15A:
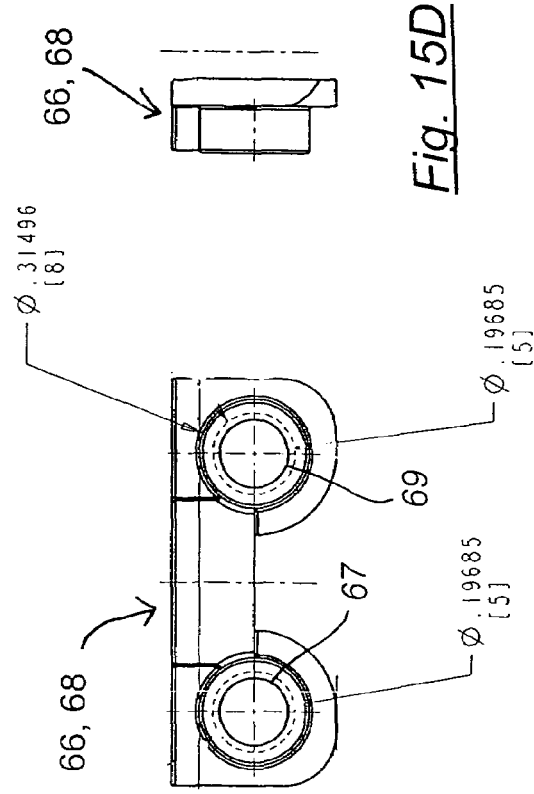
FIG. 15A is a first side view of the gear plate of the embodiment shown in FIGS. 3-14.

FIGS. 13A-13B and FIG. 14 illustrate the relationship between the guide blade 20 and the central blade 30. The central blade 30 and the guide blade 20 are perpendicular to one another, as shown in FIG. 14. One or both of them may have sharp edges, so that they are adapted to aid in cutting, and one or both cut/ream bottom B of the acetabulum, as shown in FIGS. 18A and 18B. One or both of blades 20, 30 is/are useful in moving debris (i.e. cut bone or other material) out of the way. Preferably, the radius of curvature for both the guide blade 20 and central blade 30 is designed to be the radius of the smallest hemisphere that is to be cut in the acetabulum; in this case the smallest radius of curvature is 45 mm, however other sizes may be used. As shown in FIGS. 11B and 13B, the guide blade 20 comprises channels 22, 24, which, for the preferred head 150 that expands from a diameter of 45 to 53 mm, are at a 21 degree slope, that is, at an angle 21 degrees from a plane that is perpendicular to the axis of rotation.

As shown in FIGS. 11A and 11 B, two gear plates 66, 68 threadably engage over the ends of the worms 63, 65. The gear plates 66, 68 comprise threaded cylinders 67, 69 for receiving the ends of the worms 63, 65. Preferably, the gear plates 66, 68 comprise two slightly flared edges 70, 71 for being inserted into a mortise 72, 73 (see FIG. 11A) on the cutting blades 25, 35 similar to the connection used in a dovetail joint. Other slidable connection means may be used to capture the gear plates 66, 68 in the cutting blades 25, 35, or the cutting blades 25, 35 in the gear plates 66, 68, so that as the blades 25, 35 move with the gear plates 66, 68 along the worms 63, 65.

The gear plates 66, 68 preferably move out along the worm ends 63', 63" and 65', 65" due to the rotation of the worms 63 and 65 and the threaded engagement of cylinders 67 and 69 and worm threads. The preferred worm gear 60 is a 3.58 degree, right-hand, one-lead worm gear, with toothed surface 161, but other worm gears 60 and cooperating worms 63, 65 could be used. When the knob 40 is turned clockwise (as viewed in FIGS. 3 and 7), the ring 46 and planet gears 47, 48, and 49 turn clockwise, and the sun gear 50 and rod 15 turn counterclockwise. Therefore, worm gear 60 turns counterclockwise (see FIGS. 3 and 11A), worm 63 rotates counterclockwise (FIG. 10A) and worm 65 rotates clockwise (FIG. 10A). Thus, the worm gear 60 rotates the worms 63, 65 in opposite directions and the threaded ends 63', 63" and 65', 65" of the worms push both blades 25, 35 outward. The preferred planetary transmission and worm gear system allows the reverse actions to be done, that is, turning the knob 40 counterclockwise, which results in the worm gear 60 rotating clockwise (FIGS. 3 and 11A), and worms 63, 65 rotating clockwise and counterclockwise, respectively (FIG. 10A), to retract the gear plates 66, 68 and blades 25, 35 in toward he central axis of the device. Likewise, the indicator disk 52 will move in the opposite direction to indicate the retraction of the blades.

The slidable connection between the mortises 72, 73 and edges 70, 71 and the apertures 74, 75 allow the blades 25, 35 to slide up relative to the gear plates 66, 68 (guided by the channels 22, 24 in the guide blade 20) as the gear plates carrying the blades are moved outward. Both cutting blades 25, 35 comprise two braces 75, 76 for strength and rigidity. Preferably, the leading edges 26, 36 of each side of the cutting blades 25, 35 are sharp to enable cutting of the acetabulum the entire time the reamer is rotating.

Referring specifically to FIGS. 16A-18B:

In use, the preferred embodiment is utilized in a hip arthroplasty, but, as discussed elsewhere in this document, other uses for this embodiment and/or for other embodiments of the invention are envisioned by the inventor. After the incision is made along the patient's hip joint, the hip joint is exposed and the femoral head is resected, which allows visualization of the acetabulum. The acetabulum is then cleared of debris and the reamer 100 is then fixed to a surgical drill and inserted in the acetabular space in order to reshape/enlarge the acetabulum. The surgeon holds the drill in one hand and the reamer 100, preferably by the handle sleeve 1, in the other hand as he drills into the acetabulum (the sleeve preferably staying motionless relative to the surgeon's hand while the rotational shaft system rotates, inside the sleeve, relative to the sleeve and the surgeon's hand).

As the leading edges 26, 36 of the cutting blades 25, 35 spin due to the rotation of the reamer head 150 by the reamer shaft 5, they cut/reshape a first, small hemisphere in the acetabulum. While the term "cut" is mainly used herein, it will be understood especially from the Background of the Invention section, that acetabulum will typically and naturally have a generally concave surface prior to the surgery, but that reshaping is usually required, especially after osteophytes and other deteriorated and diseased bone are removed from within and around the acetabulum during the first steps of the surgery. Hence, while the phrases "cut a hemisphere" or "make a hemisphere" are used, this is meant to include reshaping of an already-substantially concave/hemispherical surface.

Once the reamer 100 has made the first hemisphere it cannot cut a larger hemisphere until it is expanded. Therefore, cutting is stopped momentarily and the surgeon rotates the knob 40 relative to the rotational shaft system, which in turn expands the cutting blades 25, 35 to cut the next larger hemisphere of a size chosen by the surgeon. The surgeon continues to expand the blades 25, 35, removing subcondral bone until he has reached cancellous bone, which will grow into the prosthetic socket, and has reached the desired acetabular shape.

Figure 16E:
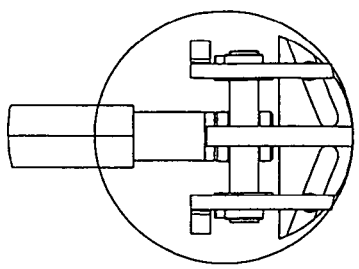
FIGS. 16A-16E are front views of the reamer head of the embodiment shown in FIGS. 3-15D, as the cutting blades are expanding (from 16A to 16E).
Figure 16D:
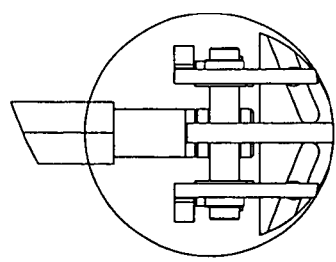
Figure 16C:
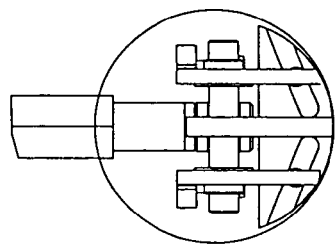
Figure 16B:
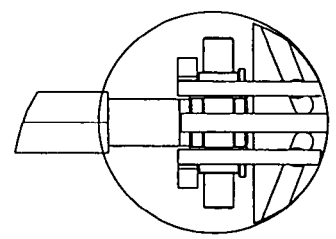
Figure 16A:
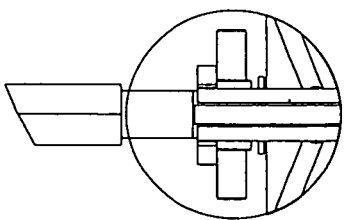

As illustrated in FIGS. 16A-16E, the preferred acetabular reamer can expand from 45 mm to 53 mm cutting diameter: FIG. 16A shows the reamer expanded to 45 mm, FIG. 16B shows the reamer expanded to 47 mm, FIG. 16C shows the reamer expanded to 49 mm, FIG. 16D shows the reamer expanded to 51 mm, and FIG. 16E shows the reamer expanded to 53 mm. While incremental expansions are shown in FIGS. 16A-16E, the expansion of the preferred embodiment is continuous rather than incremental. The inventor envisions that another reamer size will be made that expands continuously within the range of 54 mm-64 mm. The 45 mm-53 mm size reamer will work for about 80% of the patients, and the 54 mm-64 mm will accommodate the other 20%. Other reamer sizes may be manufactured as well. The expansion of the cutting blades 25, 35 may be adjusted without needing to remove the reamer head from the acetabulum. Reaming devices according to the invention may be made with gearing or other blade adjustment systems that adjust the blades continuously, incrementally, and/or even automatically.

As the blades 25, 35 expand, they are also raised along the channels 22, 24 in the guide plate by means of slide protrusions 28, 38 in the cutting blades 25, 35, which protrusions 28, 38 slide in the channels 22, 24. This properly expands the effective diameter of the reamer head while maintaining a proper cutting curvature in the lower region of the reamer head. In other words, during the expansion and rising of the blades 25, 35, they substantially follow the radius of the central blade 30 and guide blade 20 in order to maintain nearly a perfectly hemispherical shape. If the blades 25, 35 were not raised at the same time they are expanded, they would not truly be spherical segments of an effectively-spherical reamer head, and rotation of the reamer head would result in there being a raised, non-reamed ring on the otherwise generally concave surface being reamed, in the location just inward (toward the central tool axis) from the inner surfaces of the blades 25, 35. Such an incongruity would not be acceptable for hip arthroplasty, for example.

If the embodiment of FIGS. 3-15C, central blade 30 and transverse guide blade 20 are designed to define the radius of the fully-contracted reamer head, with the cutting blades 25, 35 also defining the fully-contracted reamer head radius in that they are slightly smaller in radius but also slightly distanced from the central axis of the reamer head. See FIG. 16A and schematic 17A. When the cutting blades 25, 35 begin to move out and up, they define the radius of the expanding reamer head as they become the "cutting segments" discussed earlier in this Description (see FIGS. 16B-E and also FIG. 17B). The central blade 30 and/or guide blade 20 continued to define the cutting radius of the bottom region of the reamer head (cutting/reaming bottom B region of the reamed surface), and so, because they exhibit the fully-contracted reamer head radius, there will be a very slight difference between the radius of the side S cutting edge(s) and the bottom B cutting edge(s). This difference is so small, especially until the reamer head is fully-expanded, that the reamer head effectively maintains nearly a perfect cutting sphere. A hemisphere cut by the preferred reamer is only 0.2-0.3 mm from having an absolutely perfect radius, and that is only if the reamer 100 is fully expanded (see FIG. 16E).

Due to the practical constraints of desiring a rotating shaft or other power source, and preferably a handle, connected to the reamer head, the term "cutting sphere" herein is used even through, in most embodiments, the cutting segments constructed as sharpened plates or other sharpened blades will tend not to be complete circles. Therefore the "cutting sphere" will typically, in effect, have a "spherical cap" removed or absent and the "cutting segment" will typically, in effect, have a "segment of a circle" removed or absent, to give room for the shaft, power source, handle and/or other structure. Therefore, the terms "cutting sphere," "circular," "spherical" and "spherical segment" herein do not necessarily require that the object extend 360 degrees to be exactly a complete sphere, complete segment of a complete sphere, or a complete circle.

The reamer of FIGS. 3-15C may be expanded to the extent that the slide protrusions 28, 38 reach the end of the channels 22, 24 and exit the channels 22, 24, and then the cutting blades 25, 35 will "fall-off" the gear plates 66, 68. This feature is to allow easy removal of the blades for easy cleaning. If the surgeon continues to rotate the knob 40 after the cutting blades 25, 35 have been removed, the gear plates 66, 68 will also "fall-off" the worms in order to be cleaned. While reaming the acetabulum, the surgeon will stop expanding before the point at which the cutting blades or gear plates fall off the reamer head. Alternatively, there may be stops on the ends of the worms 63, 65, or other retaining structure, to prevent the blades 25, 35 and gear plates 66, 68 from "falling off". The stops or other retaining structure would preferably be easily removable, to allow easy disassembly for cleaning and autoclaving, or for blade replacement or maintenance.

The reamer 100 reduces potential surgical injury to the soft tissue around the joint (sciatic nerve, vessels, and muscle), as well as being more efficient and more accurate than previous devices. As shown in FIGS. 18A and 18B, the reamer 100 is manufactured to be greater than 180 degrees in order to allow the reamer to cut a hemisphere even if the reamer 100 is not aligned with the axis of the acetabulum. The reamer 100 is preferably made of titanium, however other materials may be used, such as surgical steel.

While the above description focuses on expansion of the preferred reamer head, it is to be understood, and is understandable from the description and drawings, that the preferred knob and gearing system may be turned in the opposite direction to contract the size of the reamer head. During contraction of the reamer head 150, the knob 40 may be turned in the opposite direction as for expansion, the various gears will also turn in the opposite direction, and the cutting blades 25, 35 will ride on the plates 66, 68 inward toward the central axis of the device.

Cutting segments that are moveable in a direction non-parallel to the cutting segment plane, provide a head that is capable of more perfectly-spherical or perfectly-part-spherical cutting/reaming, throughout expansion, than other expandable reamers of which the inventor is aware. For example, an expandable reamer that has cutting blades that pivot outward and down in a direction parallel to the blade planes will tend to produce incongruities and/or inaccuracies in the reamed surface. Such prior art, pivoting-blade reamer heads may be designed to cut a fairly accurate hemisphere at only one configuration, for example, either when fully-contracted, or when fully-expanded, but not both.

While the preferred reaming device is especially useful for hip arthroplasty, the device may have other uses, and embodiments may be adapted for the special requirements of other uses. Further, it should be noted that it will be apparent to one of skill in the art, after viewing this Description and the Drawings, that expansion actuation systems other than the planetary and worm gear systems may be used.

In view of the above summary and detailed description, some embodiments of the reaming device may be described as comprising a reamer head; and a shaft operatively connected to the reamer head for rotating the reamer head on a reamer head axis; wherein the reamer head comprises a moveable first blade having an outer edge on a first plane that is parallel to the reamer head axis, wherein the outer edge curves preferably greater than 180 degrees on a first radius and the outer edge has at least a sharpened portion; wherein the first blade is moveable in a direction perpendicular to said first plane out away from said reamer head axis, so that the effective cutting diameter of the rotating head is increased. While it is certainly preferred that there are multiple moveable blades, to better balance the reamer head and increase total cutting edge, the broad invention includes even a single one of said moveable blades. In some embodiments, the outer edge of said first blade preferably curves between 200 and 270 degrees on said plane, but may curve different amounts. The first blade preferably is a generally circular plate.

In other embodiments, the reamer head may further comprise a moveable second blade having an outer edge on a second plane that is parallel to the reamer head axis on a side of the reamer head axis opposite from said first blade, wherein the second blade outer edge curves preferably greater than 180 degrees on a second radius and has at least a sharpened portion; and wherein said second blade is moveable in a direction perpendicular to said second plane out away from said reamer head axis. Preferably, said first radius and said second radius are equal in length. Preferably, the outer edge of the first blade curves between 200-270 degrees on said first plane and the outer edge of said second blade curves between 200-270 degrees on said second plane. Preferably, the sharpened portion of the first blade outer edge extends substantially the entire length of the outer edge, and the sharpened portion of the second blade outer edge extends substantially the entire length of the outer edge, but other lengths of portions and/or multiple portions on a blade may be used.

Preferably, the reamer head is configured to move said first blade and second blade in a direction parallel to the reamer head axis at the same time the moveable blades move outward away from said reamer head axis. The drawings and above description illustrate sloped channels as one means of accomplishing this movement diagonal to the reamer head axis, but other means may be used to index the blades to move up at the same time as moving outward.

The reamer head may comprises a transverse blade perpendicular to the first blade and having an outer perimeter curving on a transverse blade radius, wherein the reamer head is configured so that, when the first blade moves outward away from said reamer head axis and also moves parallel to the reamer head axis, a bottom edge portion of the outer edge of the first blade stays aligned with the outer perimeter of the transverse blade. Likewise, the transverse blade may be perpendicular to a second blade, so that, when the first blade and the second blade each move outward away from said reamer head axis and also move parallel to the reamer head axis, a bottom edge portion of the first blade and a bottom edge of the second blade each stay aligned with the outer perimeter of the transverse blade. Said transverse blade may extend through the reamer head axis and said outer perimeter may have a sharpened bottom portion configured to ream a bottom surface generally perpendicular to the reamer head axis. The reamer head may comprise a central blade extending through the reamer head axis and having a bottom sharpened edge configured to ream a surface generally perpendicular to the reamer head axis.

In other embodiments, the device may be described as being for forming a concave surface, the device having a cutting head rotatable on a head axis, the cutting head having a first and second blade on opposite sides of the head axis, the first and second blades being moveable outward from the head axis from a contracted position to a expanded position, wherein said first and second blade are parallel to each other and to the head axis in both the contracted position and the expanded position. The head further may comprise a third blade parallel to and extending through the head axis and having a sharpened bottom perimeter edge, wherein said first and second blades are each generally circular and each has a sharpened circumferential edge, so that, when the head is rotated on the head axis, with the first and second blades in the contracted position, the sharpened circumferential edges together with the bottom perimeter edge define a cutting sphere having a first diameter, and when the head is rotated on the head axis, with the first and second blades in the expanded position, the sharpened circumferential edges together with the bottom perimeter edge define a cutting sphere having a second diameter larger than said first diameter. Said first and second blades may have equal diameters. Said first and second blades may be configured to move upward parallel to the head axis when moving from the contracted position to the expanded position, so that said first and second blades are higher on said head in the expanded position than in the contracted position.

The devices may further comprise a shaft connected to said head coaxial with said head axis and a surgical drill operatively connected to the shaft for rotating the head to ream a bone surface.

Referring specifically to FIGS. 19-26C:

FIGS. 19-26C illustrate an alternative embodiment, wherein each cutting segment/blade moves in a direction non-parallel to its respective plane by pivoting. Each cutting segment expands outward by moving generally transversely to its plane, but, while the cutting segments of the embodiment of FIGS. 5-15C stay parallel to each other and parallel to the center axis of the device, the cutting segments of the embodiment shown in FIGS. 19-26C move transversely to their respective planes by pivoting outward. Both types of movement expand the cutting sphere by moving sphere segments farther out from the center axis. The pivoting of embodiments of the invention may be contrasted to the pivoting of blades in the prior art reaming devices, in that the prior art pivoting of blades is in a direction parallel and coplanar with the prior art blade's plane, while pivoting of blade embodiments of the invention is generally transverse to the blade's plane. Reaming device 200 has rotational shaft system that comprises a main shaft 205 comprising drill bit 210 at its top end and to the reamer head 250 at its bottom end.

Reamer head 250 comprises a transverse blade 220 fixed to the main shaft 205. Blade 220 is preferably sharpened substantially along its entire perimeter edge, so that the transverse blade and the expandable blades all cut/ream when the head 250 is fully contracted. As the expandable blades are, even in the fully-contracted configuration, slightly distanced from the rotational axis, a portion of the transverse blade edge is the sole edge for cutting/reaming the bottom B of the acetabulum, that is, in between the rotational axis of the device and the expandable blades. As the head 250 expands, a portion 221 of the sharpened edge still reams the bottom B of the acetabulum, because, in most embodiments, the expandable blades are still slightly distanced from the rotational axis, and/or the bottom edges of the pivoted blades are slightly lifted up away from the bottom B. As will be apparent to those of skill in the art, opposite sides of the transverse blade edge may be adapted as leading sides/edges or trailing sides/edges, depending upon the rotational direction of the head.

Figure 19:
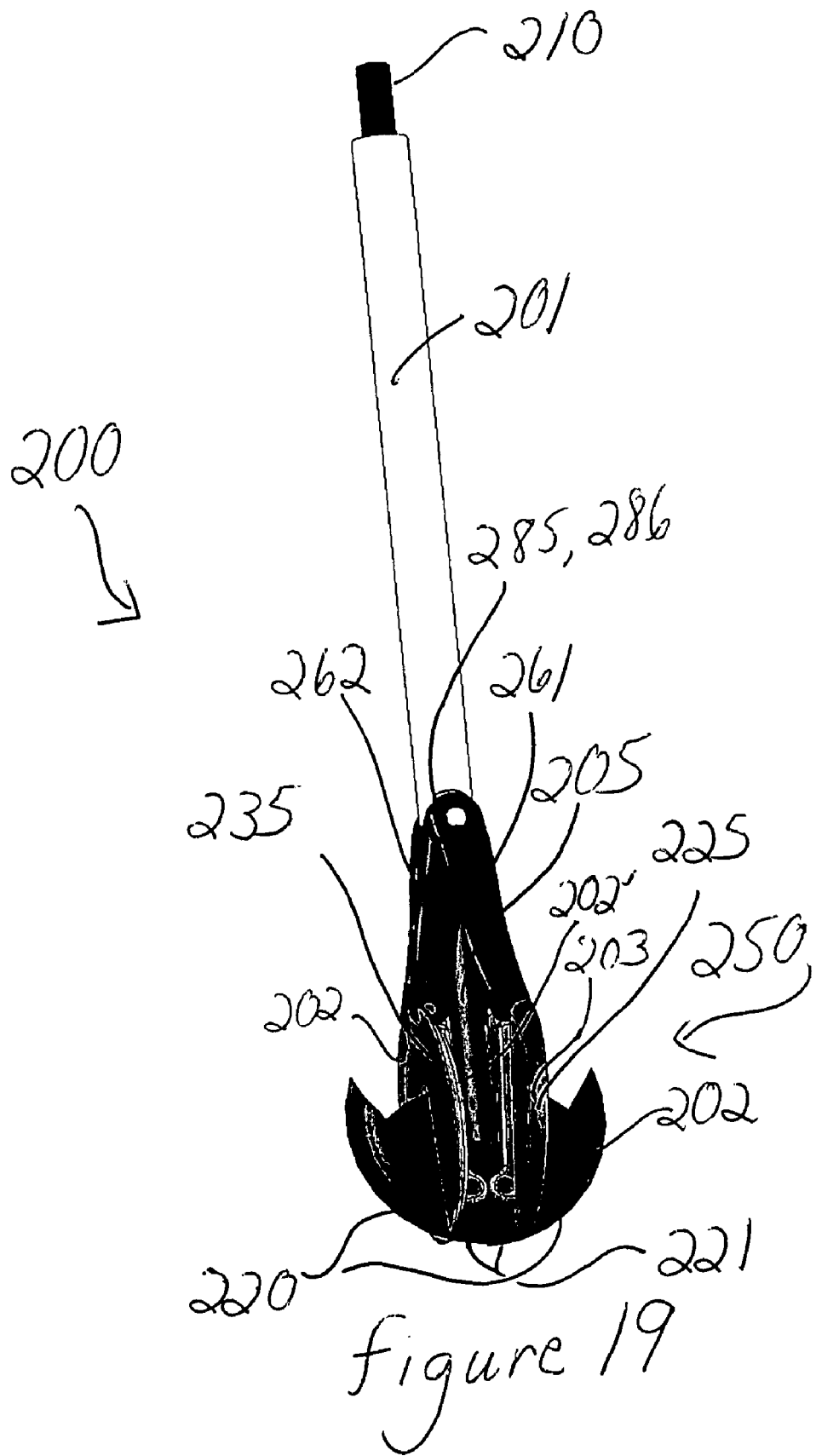
FIG. 19 is a front perspective view of an alternative embodiment of the invented reamer, with the reamer head contracted.
Figure 20:
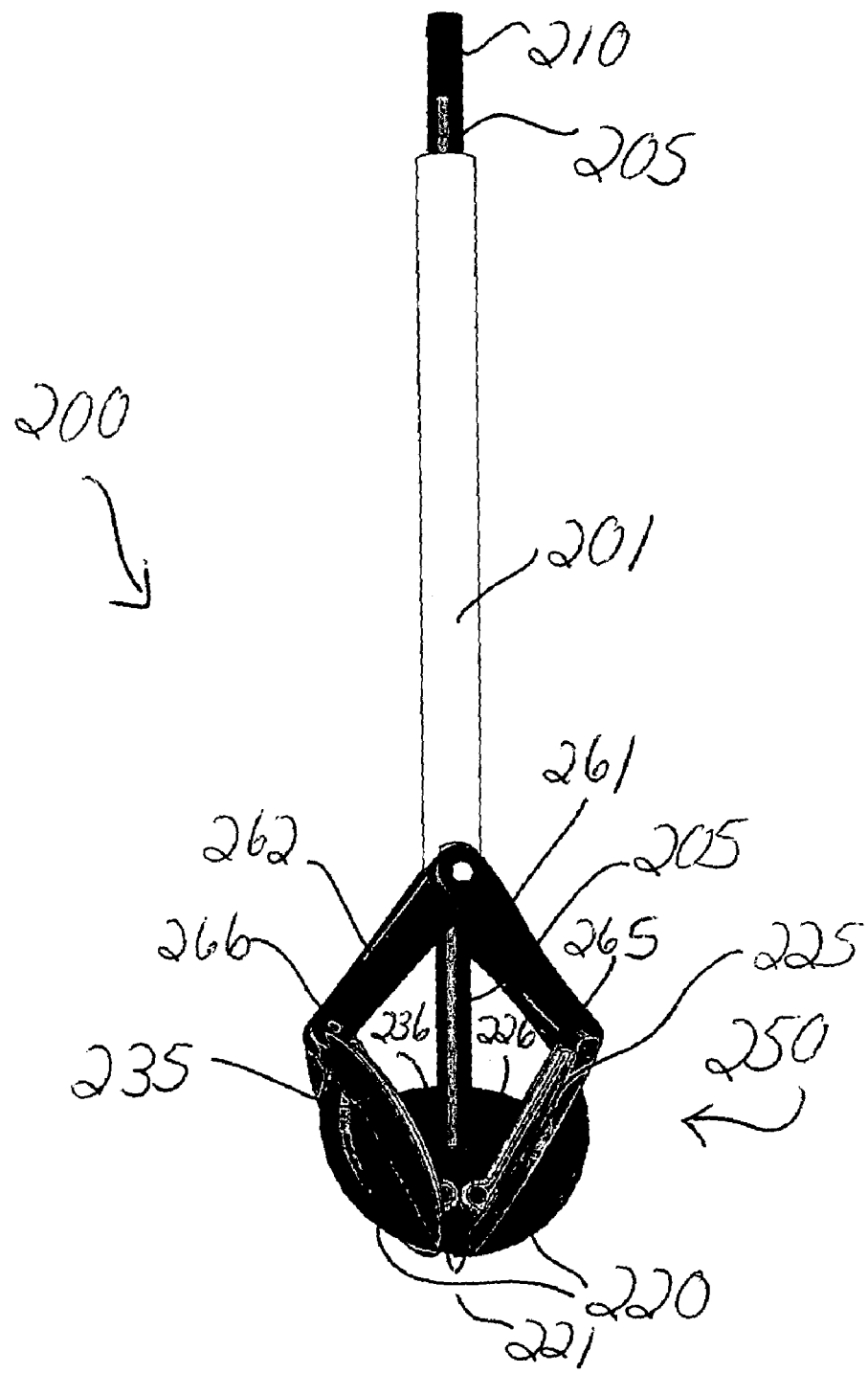
FIG. 20 is a front perspective view of the embodiment of FIG. 19, with the reamer head expanded.
Figure 21:
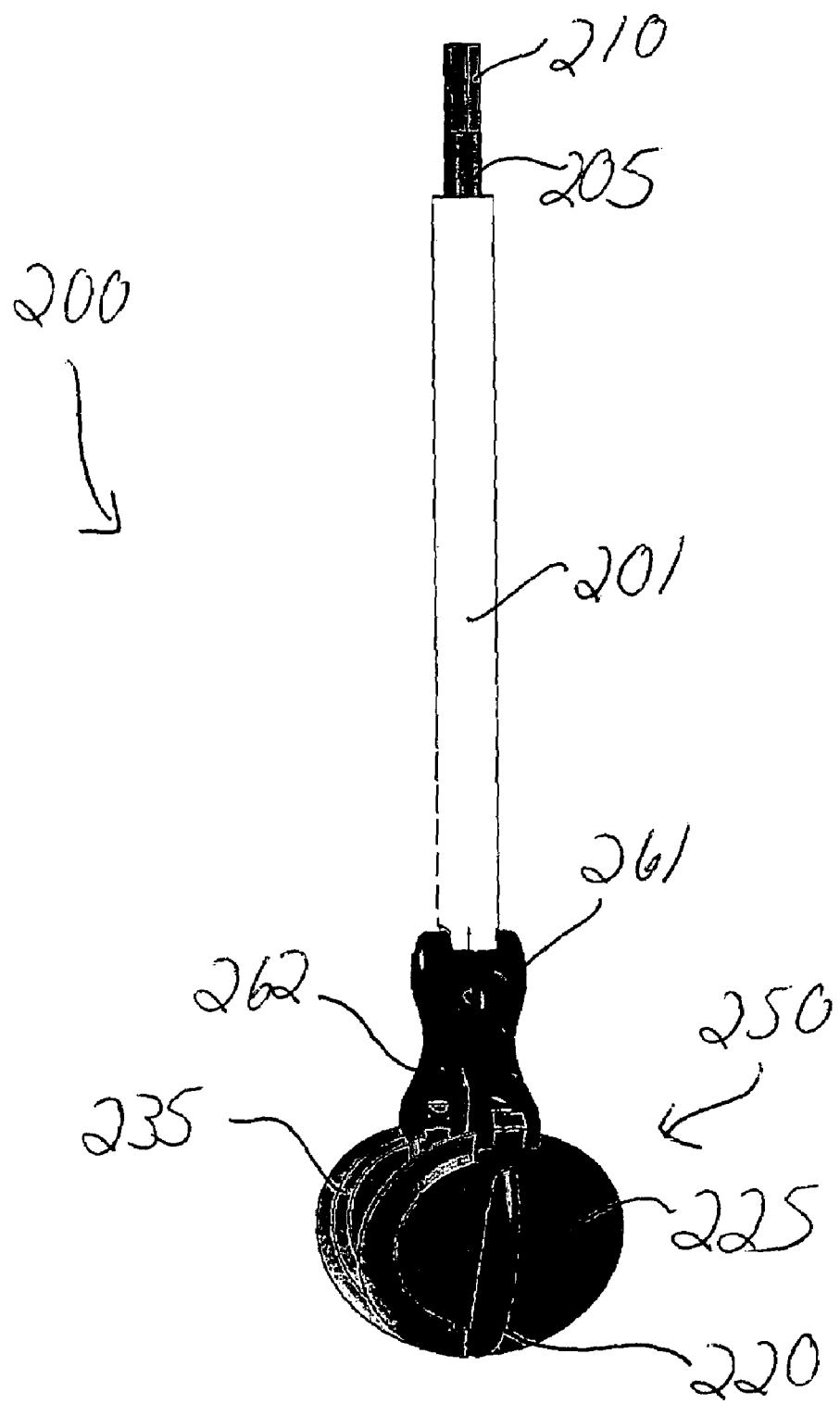
FIG. 21 is a right perspective view of the embodiment of FIGS. 19 and 20, with reamer head expanded.
Figure 22:
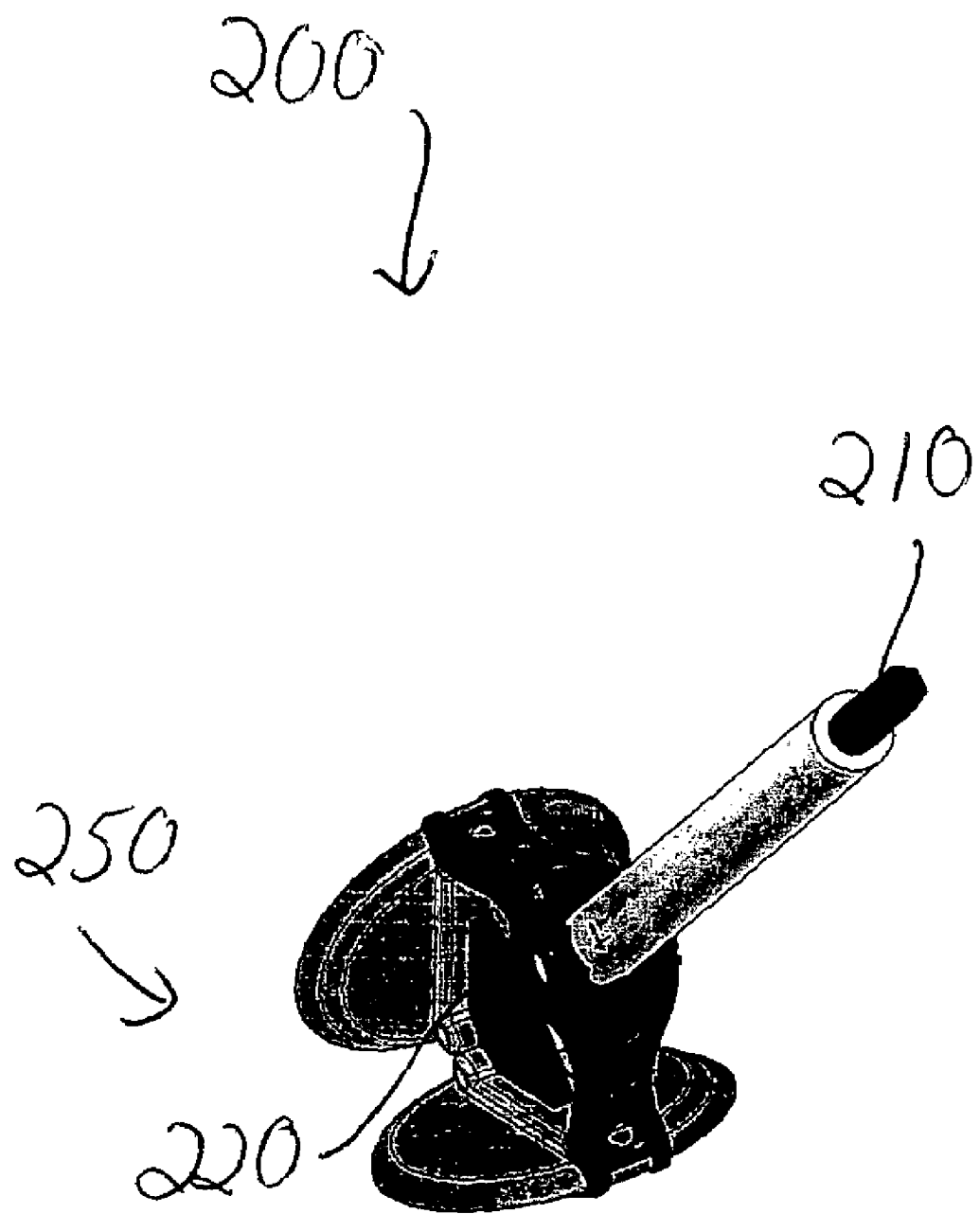
FIG. 22 is a top perspective view of the embodiment of FIGS. 19-21, with reamer head expanded.
Figure 23:
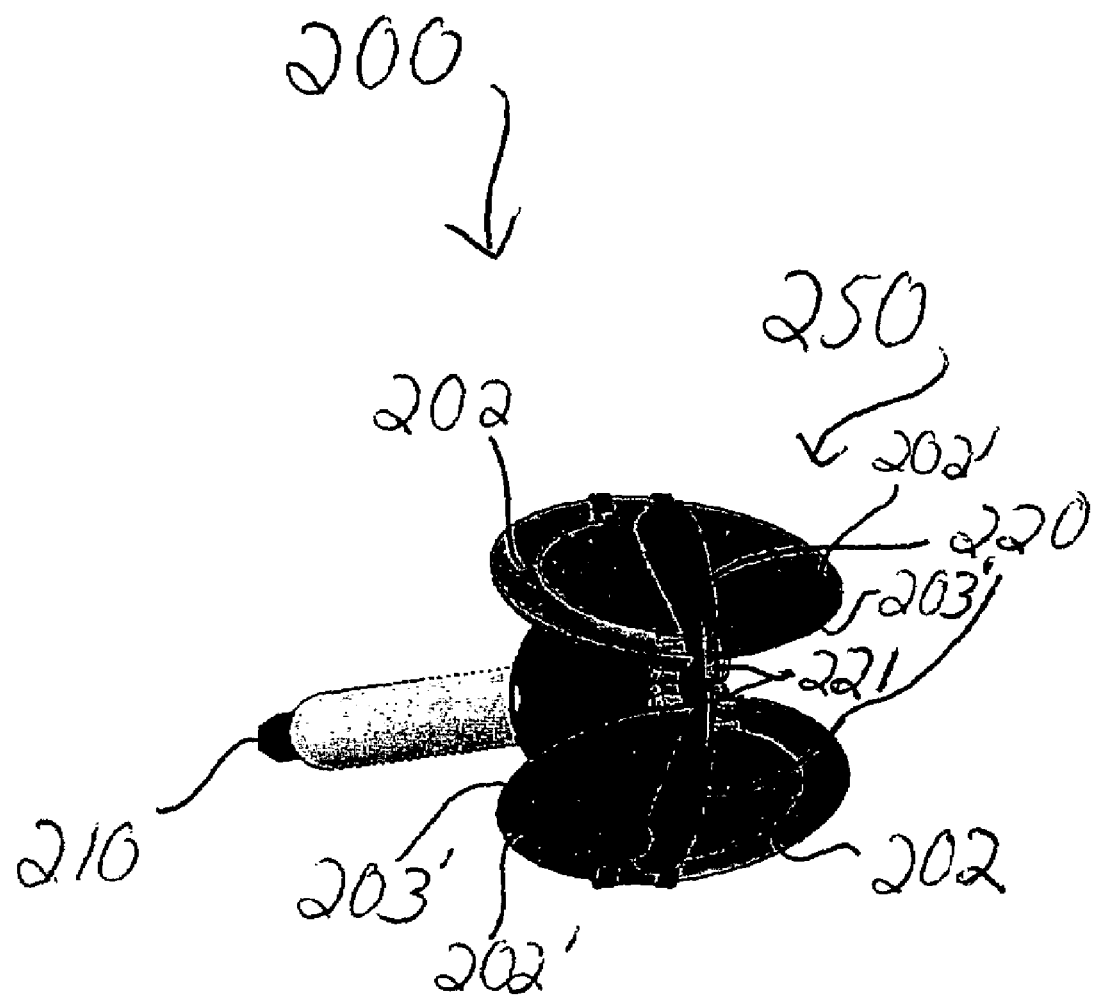
FIG. 23 is a bottom perspective view of the embodiment of FIGS. 19-22, with reamer head expanded.
Figure 24A:
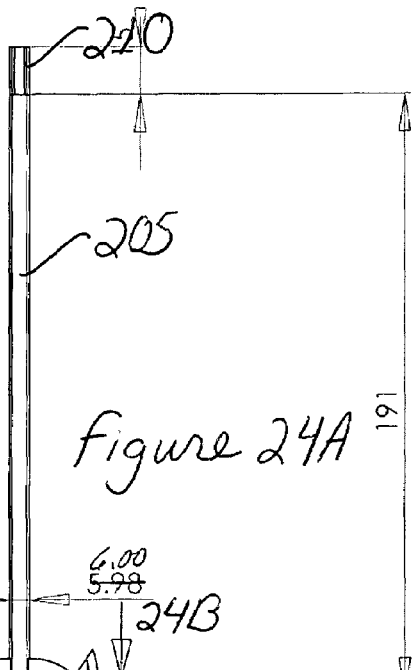
FIG. 24A is a front view of the shaft unit of the embodiment of FIGS. 19-23, which comprises a rotational shaft for connection to a power unit, and a transverse blade connected to the lower end of the rotational shaft.
Figure 24B:
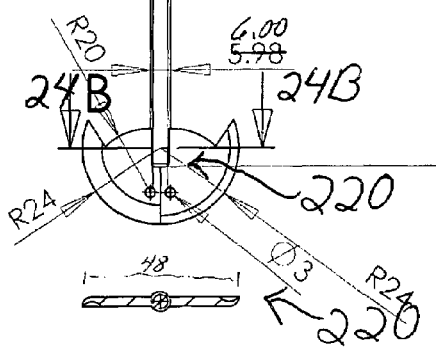
FIG. 24B is a cross sectional view of the transverse blade of FIG. 24A, viewed along the line 24B-24B in FIG. 24A.
Figure 24C:
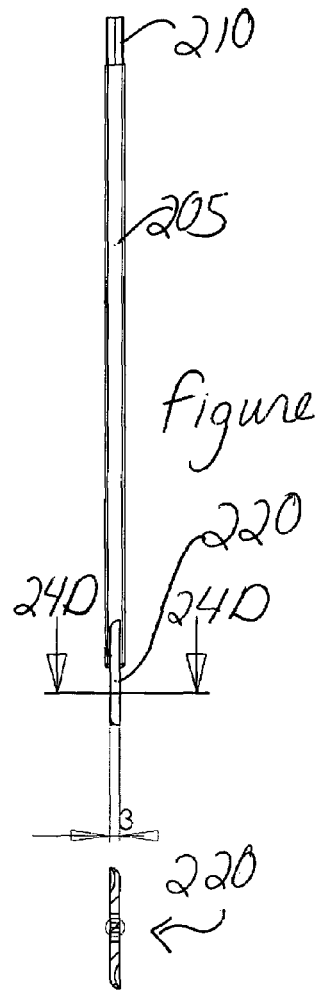
FIG. 24C is a right side view of the shaft unit of FIGS. 24A and B.
Figure 24D:
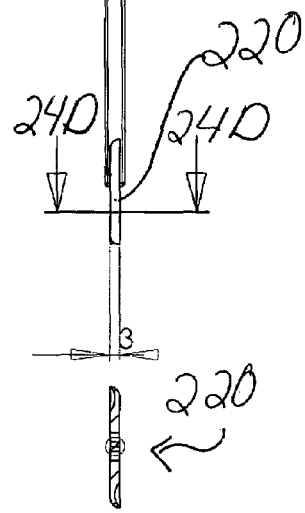
FIG. 24D is a cross-sectional view of the transverse blade of FIGS. 24A-C, viewed along the line 24D-24D in Figure FIG. 24C.
Figure 24E:
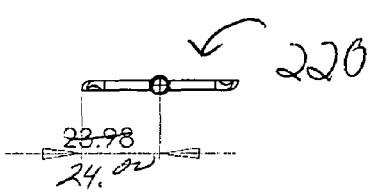
FIG. 24E is a top view of the shaft unit of FIGS. 24A-D.
Figure 26A:
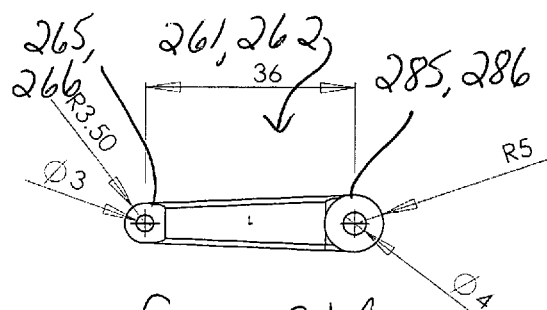
FIG. 26A is a front view of a pivot arm of the embodiment of FIGS. 19-23.
Figure 26C:
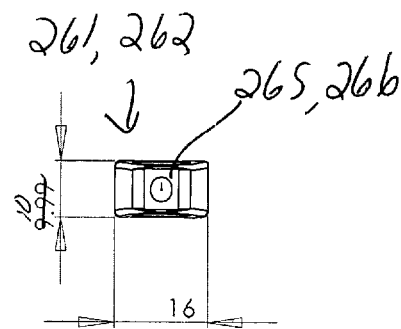
FIG. 26C is a bottom view of the pivot arm of FIGS. 26A and B.
Figure 26B:
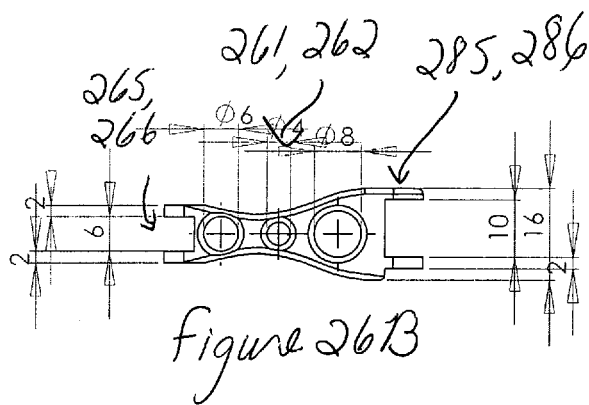
FIG. 26B is a side view of the pivot arm of FIG. 26A.

Cutting blades 225 and 235 slide on transverse blade 220, via a slot 222 in each blade receiving transverse blade 220, as they pivot from the position shown in FIG. 19 to that shown in FIG. 20. See also FIGS. 27A and B. As will be apparent to those of skill in the art, opposite sides and halves of the cutting blade edges 225, 335 may be adapted as leading sides/edges or trailing sides/edges, depending upon the rotational direction of the head. Cutting blades 225, 235 are preferably sharpened along their entire circumferences, with leading edges 202, 202' and trailing sides 203, 203' that are adapted to cut cleanly and move or "scoop" bone debris away from the blade edge and toward the center of the reamer head.

Pivot arms 261, 262 control pivoting of the blades 225, 235, which pivot arms 261, 262, in turn are controlled by a sleeve 201 sliding down the main shaft 205. Bottom ends 265, 266 of the pivot arms are pivotally connected to top brackets 275, 276 on the blades 225, 235. Top ends 285, 286 of the pivot arms are pivotally connected to the sleeve 201.

Blade pivot brackets 226, 236 connect to the transverse blade 220 and provide for the blades 225, 235 to pivot on the transverse blade 220. In this embodiment, the blades do not need to move or be ramped upwards relative to the transverse blade in order to maintain a perfect or nearly perfect cutting sphere throughout the blade expansion. Optionally, systems for pivoting the expandable blades may include some adjustment of the expandable blades upward or downward, for example, a slight adjustment downward to move the bottom edges of the expandable blades closer to the bottom edge of the transverse blade immediately adjacent the rotational axis of the device.

Various systems may be used for controlling the downward or upward sliding of the sleeve 201 relative to the main shaft 205, and/or the resulting pivoting of the pivot arms 261, 262, and, hence, pivoting of the blades 225, 235, as will be understood by one of skill in the art after reading this Description and viewing the drawings. Continuous or incremental control systems may be used, which may include an indicator to inform the surgeon of the amount of expansion of the reamer head 150.

Further, various systems may be used for allowing the surgeon to grasp the tool, while still allowing the tool to rotate in the surgeon's hand during use. An additional sleeve structure or other handle or grip (not shown) may be provided to allow grasping and guiding of the tool by the surgeon, without interfering with the reamer head rotation and with provision for access to the sleeve 201 that actuates blade expansion. Optionally, the sleeve (201) that is pushed downward for actuating the blade expansion may be adapted to also be the freely-floating sleeve or other handle during rotation of the reamer head. In such an option, some linkage or latch may be necessary to operatively connect and disconnect sleeve 201 to the pivot arms 261, 262, and/or to otherwise adapt the sleeve 201 to be both a handle that preferably does not rotate relative to the surgeon's hand and an actuator that can push down and preferably also pull up on the pivot arms 261, 262.

In use, the embodiment of FIGS. 19-26C is used much the same as the embodiment of FIGS. 5-16C. A power unit is attached to the drill bit 210, and the surgeon may begin reaming with the head 250 in the fully contracted configuration. Then, as needed, he may adjust the blades to expand the effective diameter of the cutting sphere, obtaining greater-than-hemispherical reaming capability, so that the tool's being exactly on-axis with the acetabulum axis (that is, the tool rotational axis being coaxial with the acetabulum axis) is not necessarily required. Further, with the embodiment of FIGS. 19-26C and similar pivoting-blade embodiments, the inventor has found that a perfect or nearly perfect cutting sphere may be achieved throughout the entire reaming process, with a simple and economical reaming device. The expansion system for this embodiment may be more simple and economical than that of FIGS. 3-26C, and should prove to be easy to maintain and clean, as well.

Although the blades may be described in terms of their movement relative to their "blade planes," they may also be described in terms of their movement relative to their outer perimeter edge planes or their cutting edge planes, that is, the plane that their outer perimeter edge lies one or the plane that their cutting edge lies on (with often will be the same). In many embodiments, because the blades are preferably thin plate structures, the blade plane and the outer perimeter edge plane and the cutting edge plane will be very close to each other and substantially or entirely parallel to each other, but this is not necessarily required. One of skill in the art will understand, from this Description and the Drawings, the meaning of the terms "outer perimeter edge plane" and "cutting edge plane" even though they are not specifically called out in the drawings.

Although this invention has been described above with reference to particular means, materials and embodiments, it is to be understood that the invention is not limited to these disclosed particulars, but extends instead to all equivalents within the broad scope of the following claims.

I claim:

1. A reaming device comprising:
    a reamer head;
    a shaft having an upper end and a bottom end, wherein the reamer head is operatively connected to the shaft near said bottom end for rotating the reamer head on a reamer head axis;
    wherein the reamer head comprises a moveable plate-like first blade having a blade plane that, when said first blade is in a retracted position, is generally parallel to the reamer head axis, wherein the first blade has a sharpened outer perimeter edge that curves greater than 180 degrees; and
    wherein the entire first blade is moveable, in a direction generally perpendicular to said blade plane and away from said reamer head axis, to an expanded position wherein the effective cutting diameter of the rotating head is increased, and, wherein, when said first blade moves in said direction from said retracted position to said expanded position, said blade plane remains parallel to said reamer head axis; and
    wherein the reaming device further comprises a moveable plate-like second blade on a side of the reamer head opposite said first blade, the second blade having a second blade plane that, when the second blade is in a retracted position, is parallel to the reamer head axis, wherein the second blade further has a sharpened outer perimeter edge that curves greater than 180 degrees;
    wherein said second blade is moveable, in a direction generally perpendicular to said second blade plane and away from said reamer head axis and away from said first blade, to an expanded position, wherein said second blade plane remains parallel to said reamer head axis while the second blade is expanding, so that the effective cutting diameter of the rotating head is increased; and
    wherein the entire first blade moves upwards in a direction parallel to the reamer head axis at the same time the entire first blade moves outward away from said reamer head axis and remains parallel to said reamer axis.

2. The reaming device of claim 1, wherein the entire second blade moves upward in a direction parallel to the reamer head axis at the same time said second blade moves outward away from said reamer head axis and remains parallel to said reamer axis.

3. The reaming device of claim 1, wherein the reamer head further comprises a transverse blade generally perpendicular to the first blade and having an outer perimeter curving on a transverse blade radius, wherein the reamer head is configured so that, when the entire first blade moves outward and upward, a bottom edge portion of the outer perimeter edge of the first blade stays aligned with the outer perimeter of the transverse blade.

4. The reaming device of claim 3, wherein said outer perimeter of the transverse blade comprises a sharpened bottom portion for reaming a bottom surface of a bone generally perpendicular to the reamer head axis.

5. The reaming device of claim 4, wherein the transverse blade comprises channels sloping upwards from near the reamer head axis toward the outer perimeter of the transverse blade, and wherein, wherein said entire first blade moves away from said reamer head axis and moves upwards, said first blade is guided upwards by said channels.

6. The reaming device of claim 5, wherein said channels are sloped upwards 21 degrees from a plane perpendicular to the reamer axis.

7. The reaming device of claim 3, wherein the transverse blade comprises channels sloping upwards from near the reamer head axis toward the outer perimeter of the transverse blade, and wherein, wherein said entire first blade moves away from said reamer head axis and moves upwards, said first blade is guided upwards by said channels.

8. The reaming device of claim 7, wherein said channels are sloped upwards 21 degrees from a plane perpendicular to the reamer axis.

9. A reaming device comprising:
a reamer head;
a shaft operatively connected to the reamer head for rotating the reamer head on a reamer head axis;
wherein the reamer head comprises a moveable first blade having an outer perimeter edge on a first plane that is generally parallel to the reamer head axis, wherein the outer perimeter edge curves greater than 180 degrees and has a sharpened portion; and
wherein the first blade is moveable in a direction non-parallel to said first plane and away from said reamer head axis for expanding the reamer head, said first blade pivoting out from the reamer head axis generally perpendicularly to said first plane, so that the first blade top edge moves out away from the reamer head axis to increase the effective cutting diameter of the rotating head;
the reaming device further comprises a moveable second blade on a side of the reamer head opposite said first blade, the second blade having an outer perimeter edge on a second plane that is parallel to the reamer head axis, wherein the second blade outer perimeter edge curves greater than 180 degrees and has a sharpened portion;
wherein said second blade is moveable in a direction non-parallel to said second plane and away from said reamer head axis, by being pivotal out from the reamer head axis in a direction generally perpendicular to said second plane, so that the effective cutting diameter of the rotating head is increased; and
wherein the reamer head further comprises a transverse blade generally perpendicular to the first blade and generally perpendicular to the second blade, wherein said first and second blades each comprise a slot which receives said transverse blade and each slide along said transverse blade when pivoting away from said reamer head axis.

10. The reaming device of claim 9, wherein said transverse blade extends through the reamer head axis and said transverse blade outer perimeter has a sharpened bottom portion configured to ream a bottom surface generally perpendicular to the reamer head axis.

11. A reaming device comprising:
a reamer head;
a shaft operatively connected to the reamer head for rotating the reamer head on a reamer head axis;
wherein the reamer head comprises a moveable first blade having an outer perimeter edge on a first plane that is generally parallel to the reamer head axis, wherein the outer perimeter edge curves greater than 180 degrees and has a sharpened portion;
wherein the first blade is moveable in a direction non-parallel to said first plane and away from said reamer head axis for expanding the reamer head, so that the effective cutting diameter of the rotating head is increased;
wherein said first blade is moveable in said direction by being moveable perpendicular to said first plane, and wherein said first blade remains generally parallel to said reamer head axis during said expanding, and wherein the reamer head is configured to move said first blade upwards in a direction parallel to the reamer head axis at the same time the first blade moves outward away from said reamer head axis; and
wherein said reaming device further comprises a moveable second blade on a side of the reamer head opposite said first blade, the second blade having an outer perimeter edge on a second plane that is parallel to the reamer head axis, wherein the second blade outer perimeter edge curves greater than 180 degrees and has a sharpened portion;
wherein said second blade is moveable in a direction non-parallel to said second plane and away from said reamer head axis by being moveable in a direction perpendicular to said second plane while remaining parallel to said reamer head axis, so that the effective cutting diameter of the rotating head is increased; and
wherein the reamer head further comprises a transverse blade generally perpendicular to the first blade and having an outer perimeter curving on a transverse blade radius, wherein the reamer head is configured so that, when the first blade moves outward and upward, a bottom edge portion of the outer edge of the first blade stays aligned with the outer perimeter of the transverse blade; and
wherein said transverse blade extends through the reamer head axis and said transverse blade outer perimeter has a sharpened bottom portion configured to ream a bottom surface generally perpendicular to the reamer head axis.

12. The reaming device of claim 11, wherein the reamer head is configured to move said second blade upwards in a direction parallel to the reamer head axis at the same time the second blade moves outward away from said reamer head axis; and wherein the reamer head is configured so that, when the second blade moves outward and upward, a bottom edge portion of the outer edge of the second blade stays aligned with the outer perimeter of the transverse blade.

* * * * *